(12) United States Patent
Claussen et al.

(10) Patent No.: US 8,715,981 B2
(45) Date of Patent: May 6, 2014

(54) ELECTROCHEMICAL BIOSENSOR

(75) Inventors: Jonathan Clay Claussen, Lafayette, IN (US); Aaron D. Franklin, Croton on Hudson, NY (US); Timothy S. Fisher, West Lafayette, IN (US); D. Marshall Porterfield, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 785 days.

(21) Appl. No.: 12/694,876

(22) Filed: Jan. 27, 2010

(65) Prior Publication Data

US 2010/0285514 A1    Nov. 11, 2010

Related U.S. Application Data

(60) Provisional application No. 61/147,621, filed on Jan. 27, 2009, provisional application No. 61/164,235, filed on Mar. 27, 2009, provisional application No. 61/250,776, filed on Oct. 12, 2009.

(51) Int. Cl.
| | | |
|---|---|---|
| *C12N 11/00* | (2006.01) | |
| *C12N 11/14* | (2006.01) | |
| *C12N 9/02* | (2006.01) | |
| *C12N 9/00* | (2006.01) | |
| *C12N 9/04* | (2006.01) | |
| *C12N 13/00* | (2006.01) | |
| *C12M 1/00* | (2006.01) | |
| *C25B 11/00* | (2006.01) | |
| *C12Q 1/26* | (2006.01) | |

(52) U.S. Cl.
USPC ........ 435/174; 435/136; 435/173.1; 435/183; 435/189; 435/190; 240/193; 240/194; 240/403.01; 240/403.04; 240/403.1; 240/403.11; 240/403.12; 240/403.14

(58) Field of Classification Search
None
See application file for complete search history.

(56) References Cited

U.S. PATENT DOCUMENTS 4,851,195 A    7/1989   Matthews et al.
(Continued)

FOREIGN PATENT DOCUMENTS

WO         03052181        6/2003
(Continued)

OTHER PUBLICATIONS

McLamore, E.S. et al. "A Self-Referencing Glutamate Biosensor for Measuring Real Time Neuronal Glutamate Flux" Journal of Neuroscience Methods, 2010, 189, pp. 14-22.*

(Continued)

*Primary Examiner* — Chris R Tate
*Assistant Examiner* — Aaron J Kosar
(74) *Attorney, Agent, or Firm* — John V. Daniluck; Brian W. Chellgren; Bingham Greenebaum Doll LLP

(57) ABSTRACT

Networks of single-walled carbon nanotubes (SWCNTs) decorated with Au-coated Pd (Au/Pd) nanocubes are employed as electrochemical biosensors that exhibit excellent sensitivity (2.6 mA $mM^{-1}$ $cm^{-2}$) and a low estimated detection limit (2.3 nM) at a signal-to-noise ratio of 3 (S/N=3) in the amperometric sensing of hydrogen peroxide. Biofunctionalization of the Au/Pd nanocube-SWCNT biosensor is demonstrated with the selective immobilization of fluorescently labeled streptavidin on the nanocube surfaces via thiol linking. Similarly, glucose oxidase (GOx) is linked to the surface of the nanocubes for amperometric glucose sensing. The exhibited glucose detection limit of 1.3_M (S/N=3) and linear range spanning from 10 μM to 50 mM substantially surpass other CNT-based biosensors. These results, combined with the structure's compatibility with a wide range of biofunctionalization procedures, would make the nanocube-SWCNT biosensor exceptionally useful for glucose detection in diabetic patients and well suited for a wide range of amperometric detection schemes for biomarkers.

30 Claims, 29 Drawing Sheets

(56) References Cited

U.S. PATENT DOCUMENTS

| | | |
|---|---|---|
| 4,935,345 A | 6/1990 | Guilbeau et al. |
| 5,246,859 A | 9/1993 | Nelson et al. |
| 5,382,417 A | 1/1995 | Haase |
| 5,993,694 A | 11/1999 | Ito et al. |
| 6,129,901 A | 10/2000 | Moskovits et al. |
| 6,139,713 A | 10/2000 | Masuda et al. |
| 6,217,828 B1 | 4/2001 | Bretscher et al. |
| 6,232,706 B1 | 5/2001 | Dai et al. |
| 6,297,592 B1 | 10/2001 | Goren et al. |
| 6,359,288 B1 | 3/2002 | Ying et al. |
| 6,465,132 B1 | 10/2002 | Jin |
| 6,489,394 B1 | 12/2002 | Andros |
| 6,566,704 B2 | 5/2003 | Choi et al. |
| 6,705,152 B2 | 3/2004 | Routkevitch et al. |
| 6,797,325 B2 | 9/2004 | Wang et al. |
| 6,855,603 B2 | 2/2005 | Choi et al. |
| 6,903,365 B1 | 6/2005 | Nihei |
| 6,998,634 B2 | 2/2006 | Cheong et al. |
| 7,037,767 B2 | 5/2006 | Hirai |
| 7,038,299 B2 | 5/2006 | Furukawa et al. |
| 7,084,002 B2 | 8/2006 | Kim et al. |
| 7,129,554 B2 | 10/2006 | Lieber |
| 7,235,159 B2 | 6/2007 | Gu et al. |
| 7,317,047 B2 | 1/2008 | Hsu |
| 7,345,296 B2 | 3/2008 | Tombler, Jr. et al. |
| 7,371,674 B2 | 5/2008 | Suh et al. |
| 7,425,487 B2 | 9/2008 | Kreupl et al. |
| 7,449,757 B2 | 11/2008 | Bradley |
| 7,452,452 B2 | 11/2008 | Ren |
| 7,456,564 B2 | 11/2008 | Song et al. |
| 7,538,062 B1 | 5/2009 | Dai et al. |
| 7,576,410 B2 | 8/2009 | Rueb et al. |
| 7,608,905 B2 | 10/2009 | Bratkovski et al. |
| 7,615,492 B2 | 11/2009 | Yang et al. |
| 7,646,045 B2 | 1/2010 | Kreupl et al. |
| 2002/0117659 A1 | 8/2002 | Lieber |
| 2003/0041438 A1 | 3/2003 | Wei et al. |
| 2003/0113713 A1 | 6/2003 | Glezer |
| 2003/0134433 A1 | 7/2003 | Gabriel |
| 2003/0143398 A1 | 7/2003 | Ohki et al. |
| 2003/0218224 A1 | 11/2003 | Schlaf et al. |
| 2004/0018587 A1 | 1/2004 | Makowski et al. |
| 2004/0023428 A1 | 2/2004 | Gole et al. |
| 2004/0065970 A1 | 4/2004 | Blanchet-Fincher |
| 2004/0091285 A1 | 5/2004 | Lewis |
| 2004/0120183 A1 | 6/2004 | Appenzeller et al. |
| 2004/0124504 A1 | 7/2004 | Hsu |
| 2004/0149979 A1 | 8/2004 | Cheong et al. |
| 2004/0158410 A1 | 8/2004 | Ono et al. |
| 2004/0200734 A1 | 10/2004 | Co |
| 2004/0245209 A1 | 12/2004 | Jung et al. |
| 2004/0253805 A1 | 12/2004 | Dubin et al. |
| 2005/0048414 A1* | 3/2005 | Harnack et al. ............ 430/322 |
| 2005/0081625 A1* | 4/2005 | Chen et al. ............ 73/335.02 |
| 2005/0112048 A1 | 5/2005 | Tsakalakos et al. |
| 2005/0112049 A1 | 5/2005 | Hofmeister |
| 2005/0167655 A1 | 8/2005 | Furukawa et al. |
| 2005/0175540 A1 | 8/2005 | Oraevsky et al. |
| 2005/0184641 A1 | 8/2005 | Armitage et al. |
| 2005/0188444 A1 | 8/2005 | Jeong et al. |
| 2005/0224779 A1 | 10/2005 | Wang et al. |
| 2005/0224888 A1 | 10/2005 | Graham et al. |
| 2005/0248256 A1 | 11/2005 | Song et al. |
| 2005/0249980 A1 | 11/2005 | Itoh et al. |
| 2005/0255313 A1 | 11/2005 | Kyotani et al. |
| 2005/0255581 A1 | 11/2005 | Kim et al. |
| 2006/0004271 A1 | 1/2006 | Peyser |
| 2006/0128088 A1 | 6/2006 | Graham et al. |
| 2006/0177952 A1 | 8/2006 | Lambertini et al. |
| 2006/0208362 A1 | 9/2006 | Dubin |
| 2006/0231946 A1 | 10/2006 | Pan et al. |
| 2006/0240238 A1 | 10/2006 | Boussaad et al. |
| 2006/0244361 A1 | 11/2006 | Kim et al. |
| 2006/0270229 A1 | 11/2006 | Corderman et al. |
| 2006/0281306 A1 | 12/2006 | Gstrein et al. |
| 2007/0042377 A1 | 2/2007 | Gao |
| 2007/0108482 A1 | 5/2007 | Bertin et al. |
| 2007/0114657 A1* | 5/2007 | Dangelo et al. ............ 257/720 |
| 2007/0208243 A1 | 9/2007 | Gabriel |
| 2007/0275499 A1 | 11/2007 | Corderman et al. |
| 2008/0017845 A1 | 1/2008 | Drndic et al. |
| 2008/0020477 A1 | 1/2008 | Pronovost |
| 2008/0094089 A1 | 4/2008 | Jung et al. |
| 2008/0097280 A1 | 4/2008 | Martin et al. |
| 2008/0102213 A1 | 5/2008 | Afzali-Ardakani et al. |
| 2008/0187764 A1 | 8/2008 | Jung et al. |
| 2008/0296562 A1 | 12/2008 | Murduck et al. |
| 2008/0296563 A1 | 12/2008 | Bourgoin et al. |
| 2009/0017284 A1 | 1/2009 | Dionigi et al. |
| 2009/0061451 A1 | 3/2009 | Achim |
| 2009/0084678 A1 | 4/2009 | Joshi |
| 2009/0183816 A1 | 7/2009 | Min et al. |
| 2009/0297913 A1 | 12/2009 | Zhang |
| 2010/0009134 A1 | 1/2010 | Drndic et al. |

FOREIGN PATENT DOCUMENTS

| | | |
|---|---|---|
| WO | 2003091486 | 11/2003 |
| WO | 2004029176 | 4/2004 |
| WO | 2004035462 | 4/2004 |
| WO | 2004087564 | 10/2004 |
| WO | 2005093872 | 10/2005 |
| WO | 2006031981 | 3/2006 |
| WO | 2006060054 | 6/2006 |
| WO | 2006135253 | 12/2006 |
| WO | 2007024323 | 3/2007 |
| WO | 2007089550 | 8/2007 |
| WO | 2008024674 | 2/2008 |
| WO | 2008094089 | 8/2008 |
| WO | 2008127293 | 10/2008 |
| WO | 2008129524 | 10/2008 |
| WO | 2009036071 | 3/2009 |
| WO | 2009073927 | 6/2009 |
| WO | 2009097357 | 8/2009 |

OTHER PUBLICATIONS

Bharathi, S and Nogami, M "A glucose biosensor based on electrodeposited biocomposites of gold nanoparticles and glucose oxidase enzyme" Analyst, 2001, 126(11), pp. 1919-1922.*
Feng, W. and Li, P. "Enzymes Immobilized on Carbon Nanotubes" Biotechnol. Adv., 2011, 29(6), pp. 889-895.*
Dale, N; Hatz, S; Tian, F; and Llaudet, E "Listening to the Brain: Microelectrode Biosensors for Neurochemicals" Trends in Biotechnology, Aug. 2005, 23(8), pp. 420-428.*
Tasis, D; Tagmatarchis, N; Bianco, A; Prato, M "Chemistry of Carbon Nanotubes" Chem. Rev. 2006, 106(3), pp. 1105-1136.*
Che et al., "Chemical Vapor Deposition Based Synthesis of Carbon Nanotubes and Nanofibers Using a Template Method," Chem. Mater., vol. 10, No. 1 (1998), pp. 260-267 Jan. 19, 1998.
Kamins et al., "Growth and Structure of Chemically Vapor Deposited Ge Nanowires on Si Substrates," Nano Lett., vol. 4, No. 3 (2004), pp. 503-506 Jan. 23, 2004.
Kikkawa et al., "Growth rate of silicon nanowires," Appl. Phys. Lett. 86, 123109, (2005), pp. 1-3 Mar. 16, 2005.
Li et al., "Highly-ordered carbon nanotube arrays for electronics applications," Appl. Phys. Lett., vol. 75, No. 3, (1999), pp. 367-369 Jul. 19, 1999.
Maschmann et al., "Parametric study of synthesis conditions in plasma-enhanced CVD of high-quality single-walled carbon nanotubes," Cabon. vol. 44 (2006) pp. 10-18 Sep. 16, 2005.
Masuda et al., "Fabrication of Gold Nanodot Array Using Anodic Porous Alumina as an Evaporation Mask," Jpn. J. Appl. Phys., vol. 35 (1996), pp. L126-L129 Jan. 15, 1996.
Persson et al., "Solid-phase diffusion mechanism for GaAs nanowire growth," Nature Materials, vol. 3, (2004), pp. 677-681 Sep. 19, 2004.
Maschmann et al., "Vertical single- and double-walled carbon nanotubes grown from modified porous anodic alumina templates," Nanotechnology 17 (2006), pp. 3925-2929 Jul. 11, 2006.
Franklin et al., "In-place fabrication of nanowire electrode arrays for vertical nanoelectronics on Si substrates," J. Vac. Sci. Technol. 825(2), Mar./Apr. 2007, pp. 343-347 Feb. 20, 2007.

(56) References Cited

OTHER PUBLICATIONS

Maschmann et al., "Lithography-Free in Situ Pd Contacts to Templated Single-Walled Carbon Nanotubes," Nano Letters (2006), vol. 6, No. 12, pp. 2712-2717 Nov. 9, 2006.
Ou et al., "Multisegmented on-dimensional hybrid structures of carbon nanotubes and metal nanowires," Applied Physics Letters 89, 243122 (2006) 4 pages Dec. 15, 2006.
U.S. Appl. No. 11/747,680, NF OA mailed Mar. 4, 2011, 7 pages.
Applicant Response, U.S. Appl. No. 11/747,680, filed Sep. 1, 2011, 25 pages.
U.S. Appl. No. 11/747,680, NF OA mailed Jan. 12, 2012, 10 pages Jan. 12, 2012.
Applicant Response, U.S. Appl. No. 11/747,680, filed May 11, 2012, 26 pages.
U.S. Appl. No. 11/747,680, FR OA mailed Sep. 5, 2012, 13 pages.
U.S. Appl. No. 12/024,635, NF OA mailed Aug. 17, 2012, 10 pages.
U.S. Appl. No. 12/025,453, NF OA mailed Oct. 4, 2011 10 pages.
Applicant Response, U.S. Appl. No. 12/025,453, filed Mar. 5, 2012, 15 pages.
U.S. Appl. No. 12/025,453, FR OA mailed Mar. 16, 2012, 10 pages.
U.S. Appl. No. 12/755,188 NF OA mailed Feb. 15, 2013, 10 pages.
Applicant Response, U.S. Appl. No. 11/747,680, filed Mar. 5, 2013, 19 pages.
Applicant Response, U.S. Appl. No. 12/024,635, filed Feb. 19, 2013, 18 pages.
Anandan et al., "Role of SAM Chain Length in Enhancing the Sensitivity of Nanopillar Modified Electrodes for Glucose Detection," Sensors 2009, vol. 9, pp. 1295-1305 Feb. 26, 2009.

\* cited by examiner

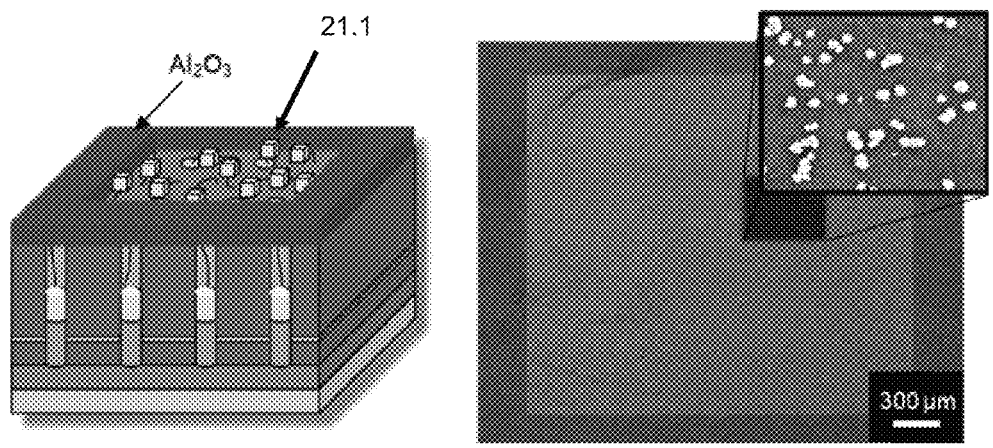
FIG. 2
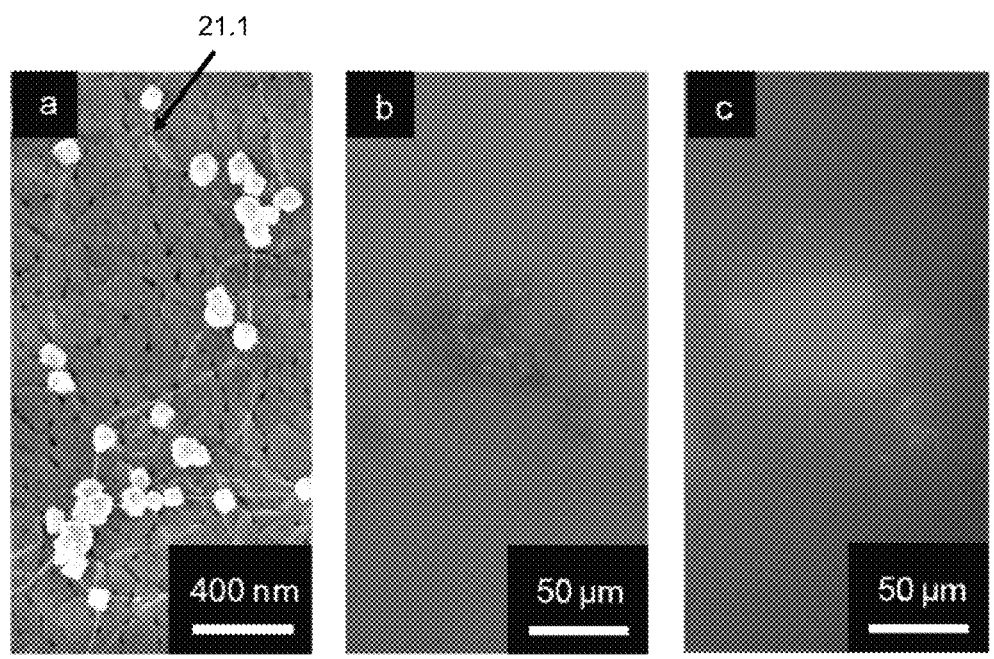
FIG. 3.1

Fig. 3.2

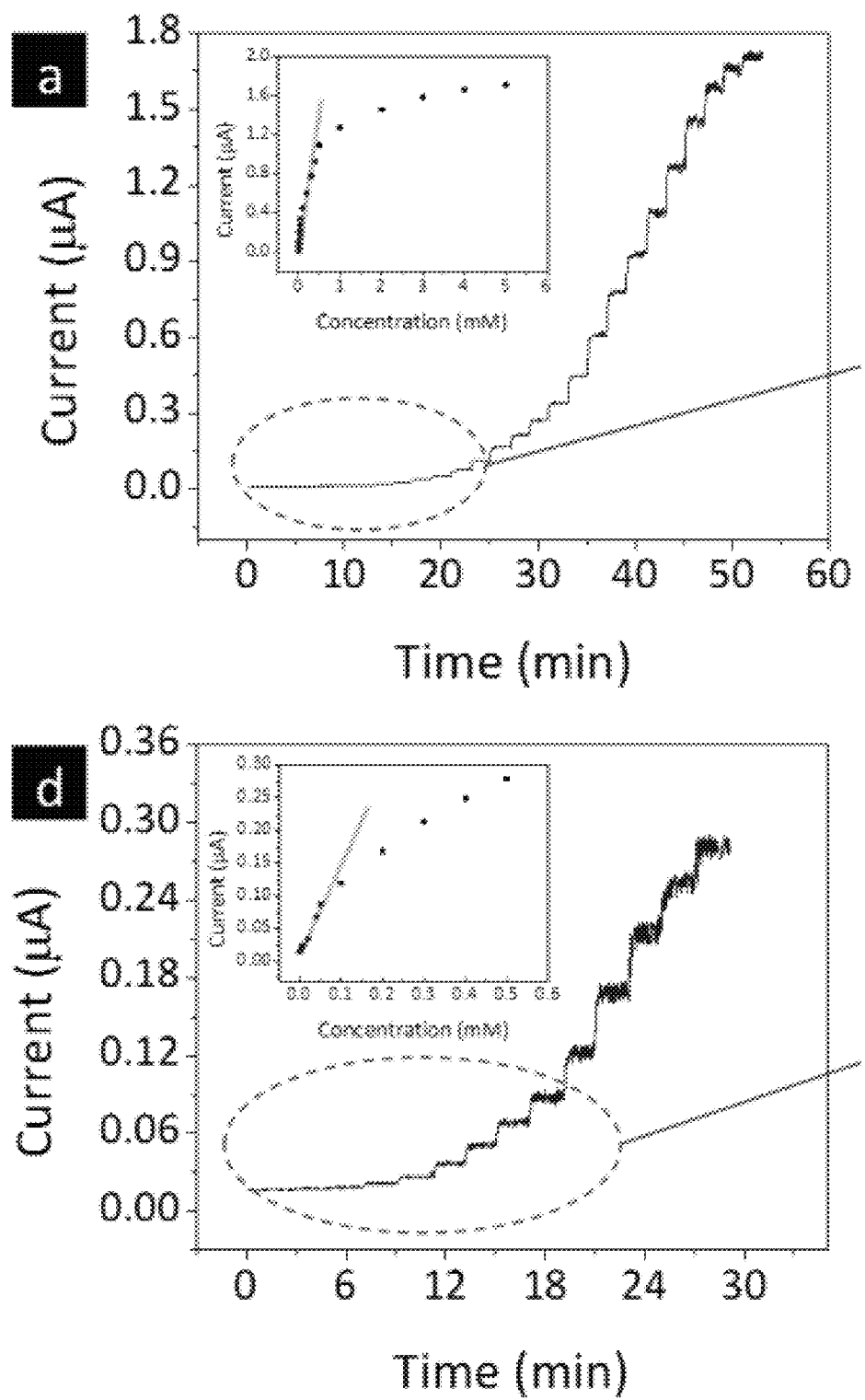
FIGS. 18(a) and (d)

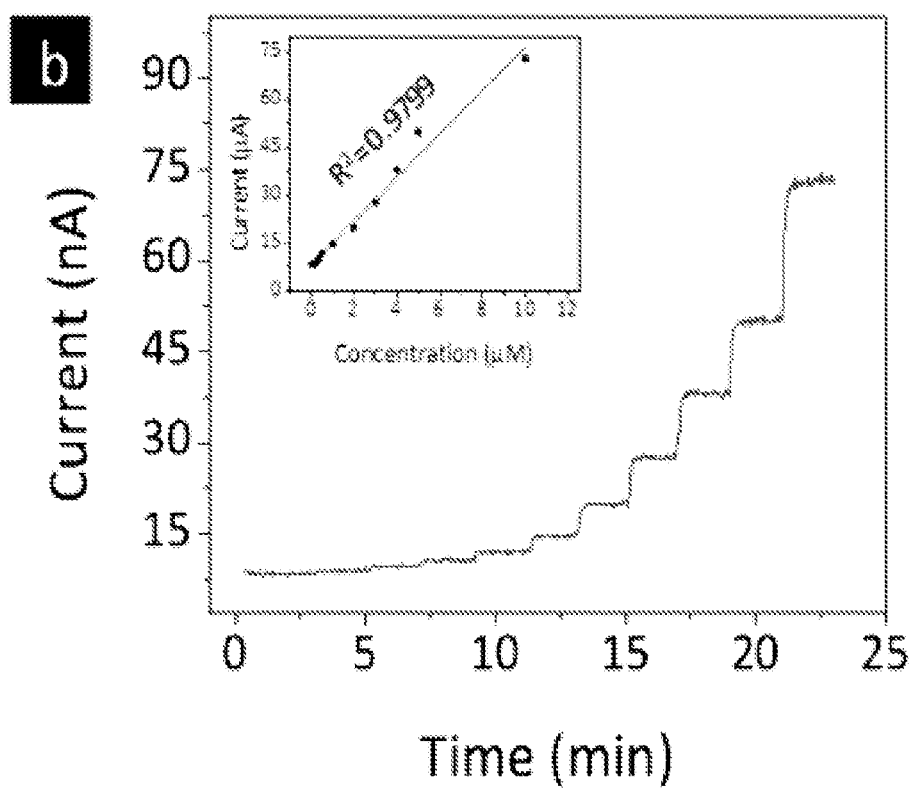
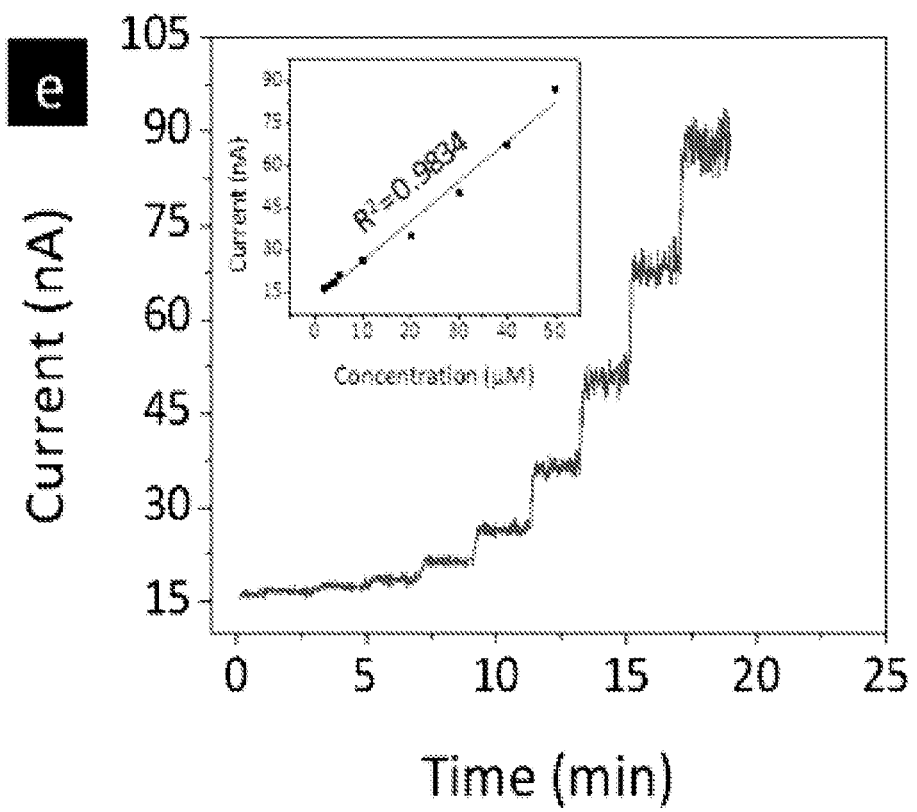
FIGS. 18(b) and (e)

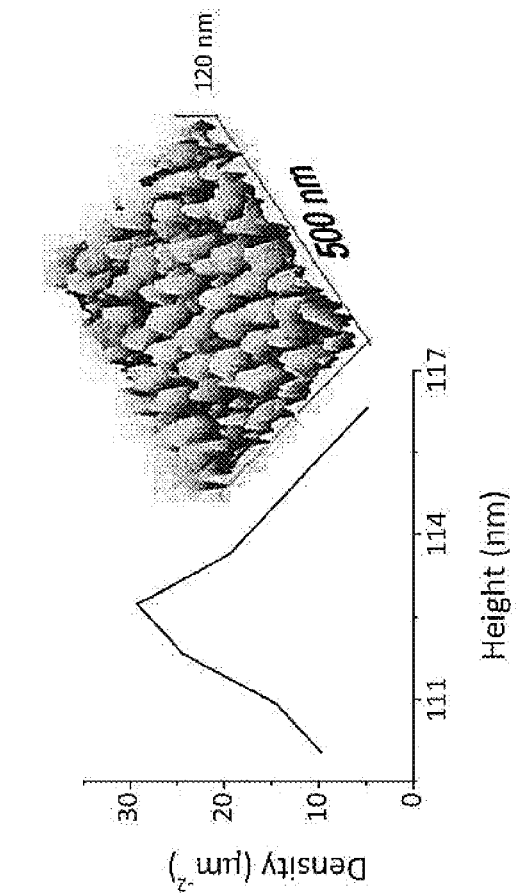
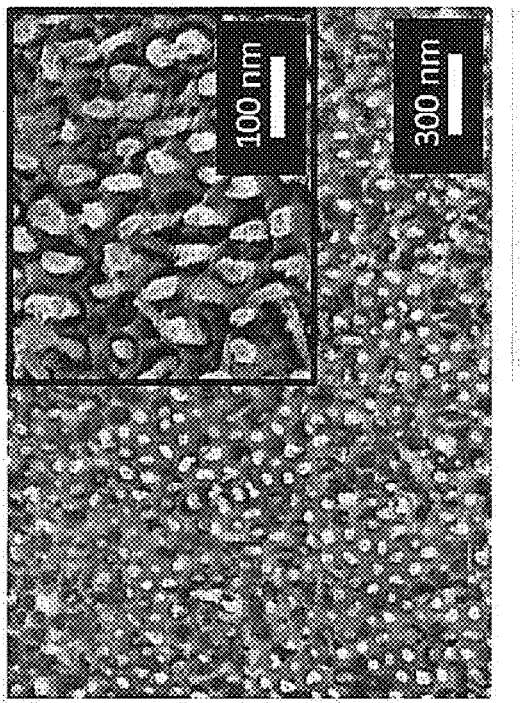
FIG. 19b

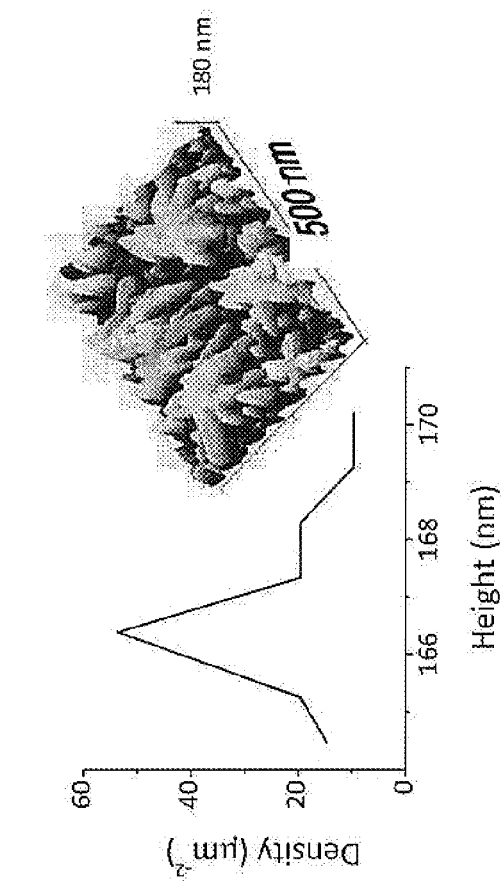
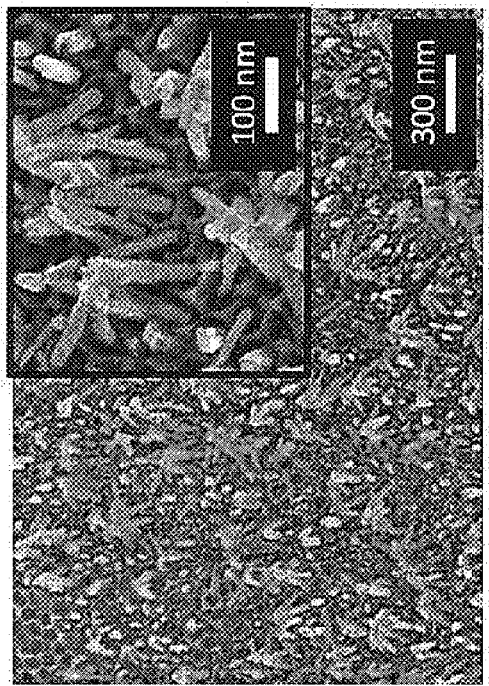
FIG. 19c

ELECTROCHEMICAL BIOSENSOR

CROSS REFERENCE TO RELATED APPLICATIONS

This application claims the benefit of priority to U.S. provisional patent application Ser. No. 61/147,621, Jan. 27, 2009, entitled NANOCUBE BIOSENSOR; U.S. provisional patent application Ser. No. 61/164,235, filed Mar. 27, 2009, entitled INSITU SYNTHESIZED GOLD NANORODS; and U.S. provisional patent application Ser. No. 61/250,776, filed Oct. 12, 2009, entitled GLUCOSE BIOSENSOR, all of which are incorporated herein by reference.

FIELD OF THE INVENTION

Various embodiments of the present invention pertain to fabrication of nanoparticles within the pores of a template, and in particular to the synthesis of a nanoscale biosensor.

BACKGROUND

Diabetic mellitus is a metabolic disease marked by high levels of blood glucose that can lead to serious complications including kidney failure, blindness, cardiovascular disease and premature death. An active glucose monitoring and control regime is required of all diabetic patients to maintain a healthy lifestyle and prevent diabetes-related complications. Furthermore, tightly controlling glucose levels in diabetic and even non-diabetic critically ill patients has shown to reduce numerous medical complications and premature death. Despite the benefits of monitoring human blood glucose levels, many home glucose monitoring systems are inaccurate—increasing the risk of serious diabetes complications. Recent reports suggest that the Food and Drug Administration is contemplating stricter standards on home glucose monitors. Thus, a glucose monitoring device with increased sensitivity towards blood glucose levels is needed to improve the prognosis of diabetics and critically ill patients and subsequently to reduce the associated health-care and medical costs. Nanotechnology-inspired biosensors have shown promising results that could achieve the highly sensitive glucose detection necessary to increase the accuracy of autonomous glucose monitoring systems.

L-Glutamate is an amino acid that acts as the primary excitatory neouro-transmitter in the central nervous system and is considered to play a fundamental role in learning, memory, locomotion, neurodevelopment, and synaptic plasticity. Abnormal levels of L-glutamate found within the neuronal and cerebrospinal fluid have been associated with numerous neurological disorders including Parkinson's and Alzheimer's disease, schizophrenia, epilepsy, and amyotrophic lateral sclerosis. Additionally, L-glutamate is utilized in the food industry as a flavor enhancer, commonly known as monosodium glutamate. Consumption of monosodium glutamate has been linked to several allegoric reactions including stomach pain, headache, and asthma.

The ability to detect glutamate concentration levels is not only of importance to the medical and biological science communities; it is of importance to the food industries as well. Furthermore, real-time ultrasensitive sensing of L-Glutamate would be useful for monitoring and treating neurological disorders. For example, monitoring L-Glutamate concentrations within neuronal fluid would greatly assist in direct electrical brain stimulation, a medical procedure that has shown promising results for the treatment of neurological disorders such as Parkinson's disease and epilepsy.

Techniques have been developed to determine the concentration of glutamate including capillary electrophoresis, mass spectrometry, and chromatographic and potentiometric titration. Though these techniques have assisted in glutamate concentration determination, they are often quite tedious and time consuming and incapable of delivering real-time sensing necessary for regulating drug delivery and other time dependent treatment plans for patients with neurological disorders. Electrochemical biosensors on the other hand offer real-time sensing of clinically important biomolecules at low-cost and minimal power requirements ideal for decentralized point-of-care facilities and implantable or hand-held devices. Nanomaterials such as carbon nanotubes and metallic nanoparticles have been utilized to improve the sensitivity and speed of electrochemical biosensors towards the sensing of DNA, proteins, and viruses.

Known SWCNT and SWCNT/metal nanoparticle glutamate biosensors show promise towards ultrasensitive glutamate sensing used in the medical, food, and biological science fields. However, immobilizing SWCNTs on glutamate biosensors often times requires chemical treating, washing, sorting and filtering that increase fabrication time and cost. Moreover, SWCNTs cast or immobilized on electrode surfaces do not ensure electrical conductivity nor are they electrically connected in parallel as individual nanoelectrodes where each CNT or metallic nanoparticle experiences diffusional independence, which can enhance electrochemical sensing capabilities.

Various chemical linking strategies have been designed in order to decorate CNTs with Pt and Pd nanoparticles. However techniques to decorate CNTs with metal nanoparticles involve chemical steps that are time consuming, and can introduce impurities into the nanoparticles or onto the CNT sidewalls that reduce the catalytic properties of the biosensor. Additionally, electrochemical CNT-based glutamate biosensors that utilize electron mediators such as ferrocene can be cytotoxic and thus would be inappropriate for in vivo or in vitro neuronal glutamate sensing devices. Furthermore enzymatic glutamate biosensors biofunctionalized with the dehydrogenase enzyme GluDH may use an external cofactor, $NAD^+$ or NADH, that is consumed during the enzymatic breakdown of the target analyte. Replenishing an enzyme cofactor in order to maintain biosensor functionality is unrealistic for in vivo neuronal biosensors.

Detection of biomolecules at low concentrations is critically important to the early diagnosis and successful treatment of diseases. Electrochemical biosensors developed with nanomaterials offer highly sensitive, realtime detection of clinically important analytes with low power requirements for decentralized testing in remote locations. For example, single-walled carbon nanotubes (SWCNTs) have enabled improvements such as (1) increased sensitivity in enzymatic electrochemical biosensors because of their inherent electrocatalytic activity toward the oxidation of hydrogen peroxide $(H_2O_2)$ and $NADH^7$ and (2) amplification of the electrochemical signal in nucleic acid biosensors and cancer biomarker immunosensors. Recently, nanomaterials, from SWCNT arrays to graphite nanoplatelets, have been decorated with metallic nanoparticles such as Pd and Pt to further increase electrocatalytic activity. Processes from exfoliation to random dispersion that limit control over the nanomaterial placement, as well as the nanoparticles' size and density, are currently used. Furthermore, these nanoparticle-decorated biosensors have limited biocompatibility and can require complex biofunctionalization schemes that increase fabrication time and cost.

What is needed are structures and processing methods that overcome some of the problems in known biosensors. Various embodiments of the present invention do this in novel and unobvious ways.

SUMMARY OF THE INVENTION

Nanomaterials such as carbon nanotubes (CNTs) and metallic nanoparticles exhibit good results in electrochemical glucose biosensing. Nano-inspired electrochemical biosensors are amenable to hand-held and implantable glucose monitoring systems because of their power requirements (<1V), response times (<10 s), and sensitivities (<1 mM). CNTs provide good electrochemical glucose sensing capabilities through their inherent ability to facilitate direct electron transfer between enzyme redox sites and to oxidize and reduce hydrogen peroxide ($H_2O_2$) and nicotinamide adenine dinucleotide (NADH), the two chemical products typically measured during enzymatic glucose sensing. Electrode materials such as Pt, Pd, and Au have been scaled down and combined with CNT-based glucose biosensors to enhance electrochemical performance and facilitate enzyme immobilization. CNT/metallic nanoparticle composite glucose biosensors have displayed good results—demonstrating high sensitivities and low detection limits useful for accurate and precise blood glucose sensing.

One aspect of the present invention pertains to an apparatus for sensing a substance. One embodiment includes a substrate including an electrically insulating layer including a plurality of pores each having a first end and second open end and a passage therebetween. Other embodiments further include a plurality of carbon nanotubes each having first and second ends, each nanotube being grown within a different one of the pores, in one end of each nanotube extending out of the second open end of the respective pore. Still further embodiments include a plurality of nanoparticles, each nanoparticle being electrodeposited to the extension of a different one of the nanotubes, each nanoparticle having bonded to it an enzyme for converting the substance into products.

Another aspect of the present invention pertains to a method of making a sensor for detecting a substance. One embodiment includes providing a substrate having a plurality of pores, growing a carbon nanotube within, and establishing parallel electrical communication among the carbon nanotubes. Still further embodiments include electrodepositing a metal nanoparticle on the portion of the nanotubes extending out of the surface and immobilizing an enzyme on the nanoparticles that converts the substance to products.

Other aspects of the present invention pertain to a method for detecting a substance. Some embodiment include providing a substrate comprising a conductive layer having two surfaces and a layer of porous anodic alumina on one surface, a plurality of the pores each including a different carbon nanotube therein. Yet other embodiments include attaching metal nanoparticles on the nanotubes. Some embodiments include providing common electrical communication by the conductive layer with each of the nanotubes. Further embodiments include bonding a catalyst that assists in the reduction-oxidation reaction of the substance to each of the nanoparticles, sensing current released from the reaction with the plurality of nanotubes.

Another aspect of some embodiments pertains to a biosensor for detecting a substance. The biosensor includes a plurality of nanoelectrodes each located within a different pore of a porous dielectric matrix material. Each nanoelectrode having a first end in electrical communication with the first end of each other nanoelectrode. The second end of each of the nanoelectrodes is sufficiently proximate the open end of its resprective pore so as to be capabable of contact with the substance. The second ends further include an attached catalyst molecule for reducing the substance to products and releasing electrons. The electrons are amperometrically sensed. The nanoelectrodes preferably include nanotubes or metal nanorods.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is excessive and unnecessary.

BRIEF DESCRIPTION OF THE DRAWINGS

FIG. 2 shows schematic and photographic representations of one embodiment of the present invention during intermediate processing operations.

FIGS. 18a and 18d are graphical representations of the electrical characteristics of the biosensors of FIGS. 13c and 13a, respectively.

FIGS. 18b and 18e are enlargements of portions of the graphs of FIGS. 18a and 18d, respectively.

FIGS. 19a, 19b, and 19c are photographic and graphical descriptions of an apparatus according to another embodiment of the present invention.

DESCRIPTION OF THE PREFERRED EMBODIMENT

Figure 1:
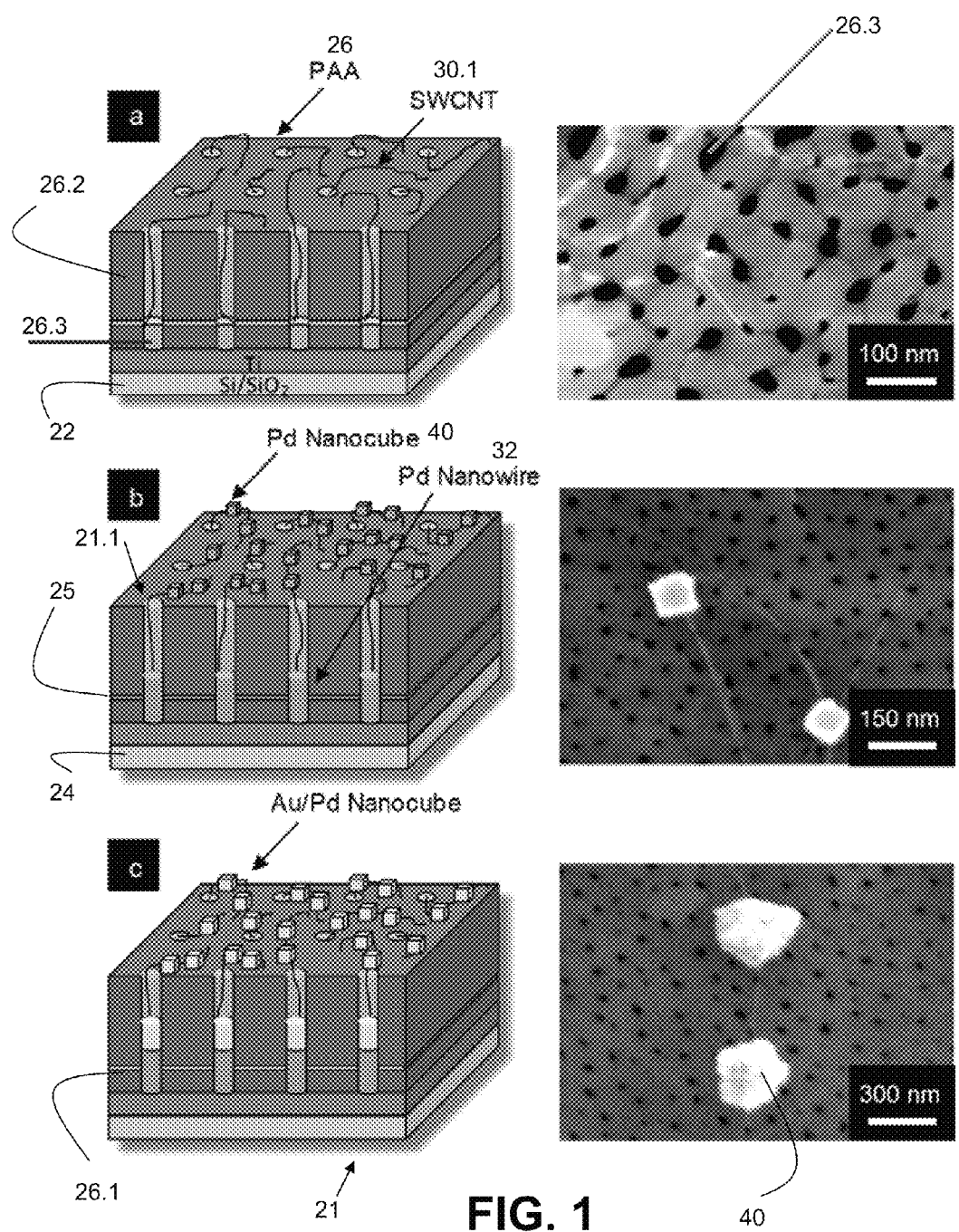
FIGS. 1a, 1b, and 1c include schematic and photographic representations of an apparatus according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, etc.) may be stated herein, such specific quantities are presented as examples only. Further, any discussion pertaining to a specific composition of matter is by example only, and does not limit the applicability of other species of that composition, nor does it limit the applicability of other compositions unrelated to the cited composition.

This application incorporates by reference the following: U.S. patent application Ser. No. 11/747,680, filed May 11, 2007, titled VERTICAL CARBON NANOTUBE DEVICE IN NANOPOROUS TEMPLATES, to inventors Maschmann, Fisher, Sands, and Bashir; U.S. patent application Ser. No. 12/024,635, filed Feb. 1, 2008, entitled CONTACT METALLIZATION OF VERTICAL CARBON NANOTUBES to inventors Franklin, Maschmann, Fisher and Sands; and U.S. patent application Ser. No. 12/025,453, filed Feb. 4, 2008, entitled CONTACT METALLIZATION OF CARBON NANOTUBES, to inventors Franklin, Maschmann, Fisher and Sands.

Various embodiments of the present invention pertain to a biosensor preferably grown from the bottom up and in-situ on an electrode. In various embodiments a porous electrically insulating layer is created on top of an electrically conductive layer. Nanoelectrodes are grown within the pores. One end of the nanoelectrodes is in electrical communication with the conductive layer; the other end of the nanoelectrodes extends out of the open end of the pore.

These nanoelectrodes can be used as biosensors by the attachment of an enzyme to the portion of the nanoelectrode extending out of the pore. In some embodiments, the enzymes are immobilized directly onto the surface of the nanoelectrode. In yet other embodiments, a nanoparticle is placed on the extension of the nanoelectrode, and the enzyme is immobilized onto the nanoparticle.

As used herein, the term immobilize refers to any method of placing an enzyme onto the surface of the nanoelectrode with sufficient tenacity to remain on the nanoelectrode during repeated usage of the biosensor. As one example, an enzyme can be immobilized by covalently bonding the enzyme to a linker molecule, and adsorbing the linked enzyme onto the surface of the nanoelectrode. In yet other embodiments, the enzyme is immobilized by any known entrapment scheme.

The nanoelectrode can be any type of nanostructure that provides good electrical communication to the conductive layer, and which further can be grown in the pore of the substrate. Examples of nanoelectrodes include single walled carbon nanotubes, multiwalled carbon nanotubes, gold nanorods, platinum nanorods, and palladium nanorods. In some embodiments, the metal nanorods are single crystal structures.

Various embodiments of the present invention include electrode and biosensor configurations that are nanostructured to provide a range of sizes, shapes, and structure of particles. Structuring permits the production of biosensors with predeterminded ranges of sensitivity, detection limits, linearity of the sensing range, and response time. Some embodiments of the present invention include the deposition of nanoparticles on the ends of the nanoelectrodes. Various embodiments of the present invention include nanoparticles having characteristic dimensions (diameter or other characteristic overall length) in the range from about 25 nanometers to about 500 nanometers. This size range has been found to provide good sensing characteristics. A preferable range is from about 100 nanometers to about 300 nanometers. Further, some embodiments of the present invention contemplate a spacing between pores of the substrate from an average of about 25 nanometers to an average of about 150 nanometers.

Various embodiments of the present invention pertain to a SWCNT-based electrochemical biosensor that utilizes Au-coated Pd (Au/Pd) nanocubes to enhance electrocatalytic activity, provide selective biofunctionalization docking points, and improve biocompatibility. The biosensor exhibits detection of a biomarker, glucose, with superior performance in comparison to other nanoscale biosensors that incorporate Au nanoparticles (AuNPs) and CNTs. Au/Pd nanocubes of homogeneous size and shape are integrated within an electrically contacted network of SWCNTs. The Pd provides a low-resistance contact between the SWCNT and Au interfaces, while the Au provides the biocompatibility for biofunctionalization, potentially with a myriad of ligands and other biomarkers. Amperometric detection of hydrogen peroxide is used for preliminary characterization of the biosensor.

To demonstrate a medical application, the Au/Pd nanocubes are selectively immobilized with glucose oxidase (GOx) via thiol linking for amperometric glucose detection. Results reveal a high sensitivity, wide linear range, and low detection limit toward glucose. These results not only illustrate the effectiveness of the nanocube-SWCNT biosensor for glucose sensing, but they also prove the utility of the biosensor's microenvironment for immobilization with vast quantities of enzyme and excellent electron transfer between the enzyme and biosensing chip. Fabrication is straightforward and scalable for integration into commercial biosensors with customized biofunctionalization for the detection of a desired molecular environment.

In yet other embodiments, there are two hybrid nanoelectrodes comprised of networks of single-walled carbon nanotubes (SWCNTs) grown in-situ from a porous anodic alumina (PAA) template decorated with Pd nanocubes and Pt nanospheres respectively, employed as electrochemical glutamate biosensors. The size and spacing of the respective metallic nanocubes and nanospheres are tuned to enhance electrochemical performance by establishing a balance between diffusional independence and electroactive surface area. The respective Pd-SWCNT/PAA and Pt-SWCNT/PAA electrodes are characterized via ferricyanide cyclic voltammetry and the effective electrocatalytic surface area, $(2.27\pm0.2)\times10^{-4}$ cm$^2$ and $(3.13\pm0.2)\times10^{-4}$ cm$^2$ respectively, is calculated by way of the Randles-Sevcik equation.

To create electrochemical glutamate biosensors, the enzyme glutamate oxidase (GluOx) is cross-linked with a 1% (w/v) bovine serum albumin (BSA) and 0.125% (w/v) gluteraldehyde solution and subsequently immobilized onto the metallic nanoparticle/SWCNT networks through a facile drop coat method. The biofunctionalized GluOx/Pt-SWCNT/PAA and GluOx/Pd-SWCNT/PAA biosensors exhibit a sensitivity of 72.4 μA mM$^{-1}$ cm$^{-2}$ and 16.8 μA mM$^{-1}$ cm$^{-2}$ respectively towards the oxidation of $H_2O_2$, the redox product of the enzymatic GluOx/L-glutamate reaction. Subsequently the GluOx/Pt-SWCNT/PAA biosensor amperometrically sensed glutamate with a sensitivity of 27.4 μA mM$^{-1}$ cm$^{-2}$ while exhibiting a wide linear sensing region extending from 50 nM to 500 μM with a theoretical detection limit of 7.6 nm (3σ). The GluOx/Pd-SWCNT/PAA biosensor portrayed a linear sensing region from 1 to 90 μM with a theoretical detection limit of 180 nM (3σ). Both sensors experience a quick sensor response time ($t_{90\%}$) of 8 seconds.

These results combined with the biosensor fabrication scheme including the in situ growth of SWCNTs, tunable size and morphology of metallic nanoparticles, and facile enzyme immobilization scheme create a biosensor that can potentially be scaled for integration into a wide range of commercial applications, including those involving the treatment of neurological disorders such as Parkinson's disease and epilepsy.

The GluOx/Pt-SWCNT/PAA biosensors 320 and 320' demonstrate that an electrochemical glutamate biosensor can be synthesized in an in situ scalable process. The in situ templated fabrication of the SWCNT arrays and the subsequent electrodeposition of metallic nanoparticles preferably does not include washing, sorting, or chemical functionalization. Furthermore the electrode was biofunctionalized by drop coating onto the nanoparticle/SWCNT arrays a stable mixture of GluOx—an enzyme that does not require cofactor replenishment during biosensor function. All of these steps can be automated and scaled to allow for mass production for integration into commercial applications. These fabrication techniques could provide a connection between biosensor research and biosensor production. Developing these SWCNT/metal nanoparticle arrays for implantable neuorological devices is plausible.

A GluOx/Pt-SWCNT/PAA biosensor according to one embodiment of the present invention amperometrically sensed glutamate with a 7.6 nm (3σ) theoretical detection limit, 50 nM to 500 μM linear sensing range, and 27.4 μA mM$^{-1}$ cm$^{-2}$ sensitivity. These results can be attributed to a number of factors including the electrocatalytic nature the of Pt towards the oxidation of $H_2O_2$, the high surface-to-volume ratio of the SWCNTs and Pt nanospheres that promotes high charge transfer, and the radial diffusion to the Pt decorated arrays of SWCNTs. Furthermore, the Pt-SWCNT arrays create a microenvironment that is good for enzyme immobilization and enzyme/biosensor charge transport, while the GluOx/BSA/gluteraldehyde biofunctionalization scheme assists in maintaining the functionality and life of the GluOx on the biosensor surface. Another aspect of this biosensor is its in situ fabrication scheme that can be automated and scaled for production and integration into commercial biosensors. GluOx/Pd-SWCNT/PAA biosensors according to various embodiments of the present invention not only display sensitive glutamate sensing capability—they display biosensor manufacturability and commercial viability for integration into implantable neurological devices for the treatment of various disorders, including Parkinson's disease and epilepsy.

Various embodiments of the present invention include a CNT/nanoparticle composite glucose biosensor that produces sensitive glucose sensing while avoiding the complex fabrication schemes that have hindered the development of nano-inspired glucose biosensors. Shown herein is a bottom-up approach to CNT growth combined with metallic nanoparticle deposition and a drop-coat biofunctionalization scheme for glucose monitoring—methods that can be scaled for integration into commercial handheld or implantable glucose sensing devices. Results from these devices are discussed and correlated to the electrochemical mechanisms involved in charge transport associated with the enzymatic breakdown of glucose.

FIRST EXAMPLE

The construction of a biosensor 20 adapted and configured for detection of a substance 10 such as D-glucose according to one embodiment of the present invention is shown in FIGS. 1a, 1b, and 1c (including both a schematic and a photographic representation of one embodiment of the invention). FIG. 1 are tilted cross-sectional schematics with corresponding top view field emission scanning electron microscopy (FESEM) micrographs portraying sequential fabrication process steps: (a) SWCNTs 30 grown from the pores 26.3 of the PAA insulating and dielectric layer 26 via MPCVD (FESEM shows a SWCNT protruding from a pore and extending along the PAA surface), (b) electrodeposition of Pd to form Pd nanowires 32 in pores and Pd nanocubes 40 on SWCNTs (two such nanocubes are shown in corresponding FESEM), and (c) electrodeposition to coat the existing Pd nanocubes with a thin layer of Au.

One step in the fabrication of some nanocube-SWCNT biosensors in various embodiments involves the fabrication of a porous anodic alumina (PAA) supporting template for SWCNT growth. The PAA templates include pores with an average diameter and pitch of 20 and 100 nm, respectively. SWCNTs 30 nucleate within the pores 26.3 and grow vertically until they protrude from their pore and extend laterally along the PAA surface, creating a low density, interlacing network (FIG. 1a). Although nanotubes 30 can be considered to grow vertically, it is appreciated that the nanotubes can also be considered to grow within parallel pores of any orientation, and further that the pores are substantially perpendicular, in one embodiment, to a conductive layer 24.

Low density SWCNT arrays, where individual tubes 30 act as distinct nanoelectrodes 21 after being placed in electrical communication with conductive layer 24, exhibit higher sensitivities and lower detection limits than macroscale carbon paste or SWCNT thin film electrodes. The low density, horizontal portions of the SWCNTs on the PAA surface allow biomolecules to reach the SWCNT sidewalls unabated for detection and also permit controlled electrodeposition of metallic nanocubes on the SWCNT surfaces. Furthermore, this facile in situ fabrication process allows for the attainment of controlled-density SWCNT networks, whereas SWCNT thin film electrodes and SWCNT paste electrodes offer little density control and often include complex SWCNT processing steps.

To provide docking ports for enzymatic functionalization, Au/Pd nanocubes 40 are electrodeposited onto the SWCNTs. In one embodiment of the present invention, the nanocubes are produced by first electrodepositing Pd into the PAA, which forms Pd nanowires 32 within the pores 26.3 that provide electrical contact to the SWCNTs, thus adding the SWCNTs to the electrochemical electrode—conductive layer 24 and causing well-defined Pd nanocubes 40 to form at the SWCNT defect sites (see FIG. 1b). A low resistance contact is created at the SWCNT Pd interface because of the high work function and wetting capabilities of Pd with SWCNTs.

Following the fabrication of the Pd nanocube decorated SWCNTs, Au is electrodeposited to provide a thin layer that coats the existing nanocubes 40 (see FIG. 1c). This capping layer of Au, with its inherent resistance to oxidization and chemical fouling, creates an interface that is amenable to biofunctionalization with a wide range of biomarkers and chemical ligands. Furthermore, Au nanoparticles provide glucose sensing because they act as an electrocatalyst in the oxidation/reduction of $H_2O_2$ are excellent electrical conductors, and to promote direct electron transfer between the enzyme and electrode surface.

Another step for fabricating the nanocube-augmented SWCNT biosensors 20 involves definition of the electrode area. Surface area definition is accomplished by lithographically patterning the nanocube-SWCNT electrode 21 to protect the active region while $Al_2O_3$ is electron-beam evaporated to inactivate the remainder of the template as illustrated in FIG. 2.

FIG. 2 is a tilted cross-sectional schematic and corresponding FESEM micrographs portraying deposited $Al_2O_3$ to define controlled electrode surface area. The FESEM micrograph shows lithographically patterned $Al_2O_3$ on the top surface of the nanocube-SWCNT electrode 21 (comprising a plurality of individual nanoelectrodes 21.1), with an inset showing a magnified view of Au/Pd nanocubes and SWCNTs on the PAA surface. Defining the surface area of the electrode enables variation of the sensitivity for optimization of the signal-to-noise ratio.

In one embodiment, a rectangular window (such as 4 mm by 4 mm) of photoresist (such as AZ151A) is placed on the surface of the sensor. Then, the alumina is e-beam evaporated over the surface of the sensor. The sensor is then soaked in acetone overnight. This acetone soak lifts off the lithographically applied photoresist, and with it the corresponding layer of alumina is also removed. This process exposes an electrochemically active region on the sensor of the same size as the photoresist pattern.

To verify the biofunctionalization capability of the Au/Pd nanocubes, thiolated biotin ligands are coupled to the biosensor. The complementary protein of biotin, streptavidin, is subsequently fluorescently labeled and captured by the biotin-coupled Au/Pd nanocubes. Fluorescence microscopy is used to characterize the selective binding of fluorescently labeled streptavidin to the biotin-coupled Au/Pd nanocubes (FIG. 3.1).

Figure 3:
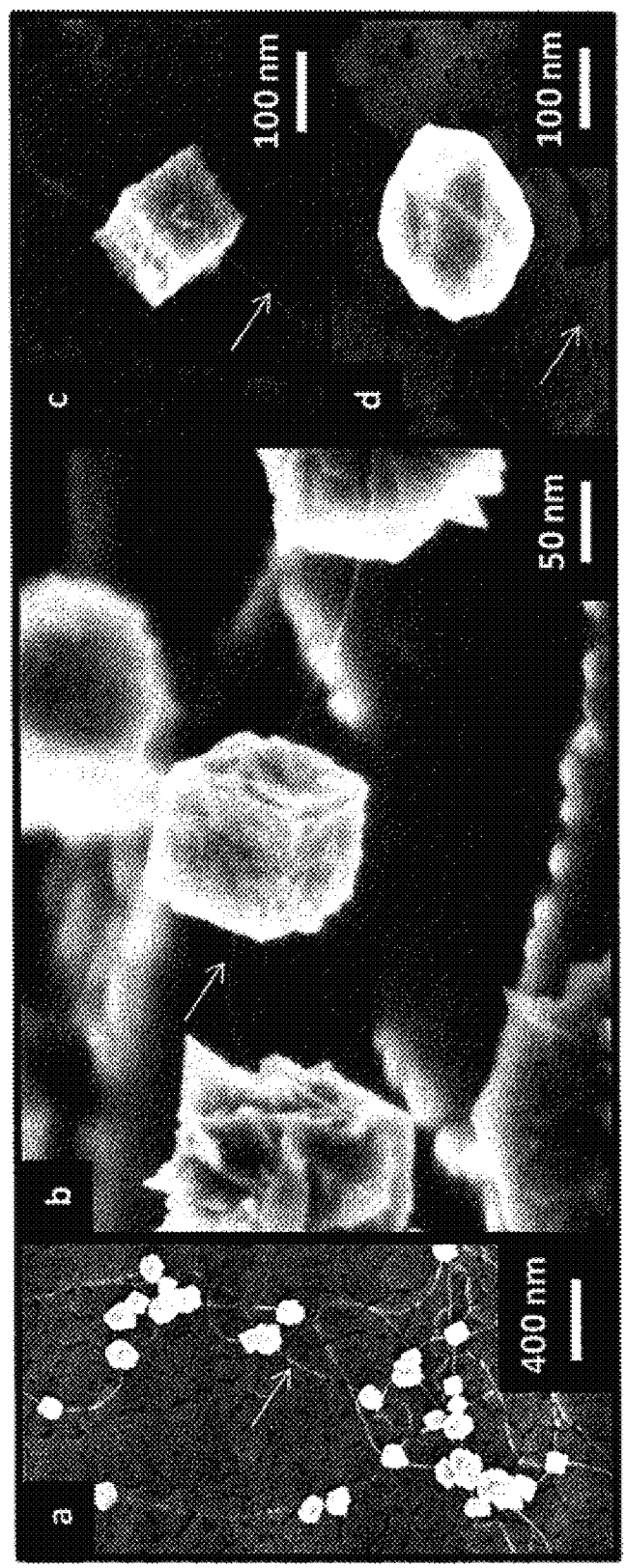
FIGS. 3.1a, 3.1b, and 3.1c are photographic representations of an apparatus according to one embodiment of the present invention FIGS. 3.2a, 3.2b, and 3.2c are photographic representation according to one embodiment of the present invention.

FIG. 3.1 show: (a) high-magnification FESEM micrograph portraying a cluster of Au/Pd nanocubes connected by SWCNTs on the Au/Pd nanocube-SWCNT biosensor surface. (b) Optical micrograph portraying a large region of Au/Pd nanocube 40 clusters and (c) fluorescence micrograph of the same region demonstrating the specific capture of Alexa-488 labeled streptavidin on the biotin functionalized Au/Pd nanocube clusters.

FIGS. 3.2a, b, and c show FESEM micrographs portraying (a) cluster of Au-coated Pd nanocubes connected by a network of SWCNTs (arrow), (b) a Pd nanocube 40 suspended and fully supported by a SWCNT 30 (arrow), (c) a single Pd nanocube with SWCNT (arrow) and (d) a Au-coated Pd nanocube 40 with SWCNT 30 (arrow).

To demonstrate the efficacy of the nanocube-SWCNT biosensor 20, hydrogen peroxide ($H_2O_2$) is used as a control system to perform several amperometric experiments via a three-electrode setup in 20 mL of phosphate buffer solution (PBS) at pH 7.4. The biosensor serves as the working electrode, a platinum wire as the auxiliary electrode, and an Ag/AgCl wire as the reference electrode. All tests involve detection of the redox current associated with the oxidation of peroxide at a working potential of 0.5 V and successive increases in concentration of 10 $\mu M H_2O_2$. A control experiment is run for comparison; a sample with bare SWCNTs in PAA with no decoration with Pd or Pd/Au nanocubes. As shown in FIG. 4a, the bare SWCNT electrode experiences virtually no increase in current with each successive addition of $H_2O_2$.

FIGS. 4a and 4b are graphs pertaining to amperometric sensing of $H_2O_2$ oxidation (0.5 V) in 20 mL of PBS (pH 7.4) using a three electrode potentiostat. The biosensor was tested by increasing the concentration of $H_2O_2$ by 10 mM (a) for the bare SWCNTs on PAA, Pd nanocube-SWCNT on PAA, and Au/Pd nanocube-SWCNT on PAA electrodes. The resulting data was processed and plotted as a scatter plot (current vs concentration) with linear regression analysis (b) for the Pd nanocube-SWCNT on PAA and the Au/Pd nanocube-SWCNT on PAA electrodes.

Figure 4:
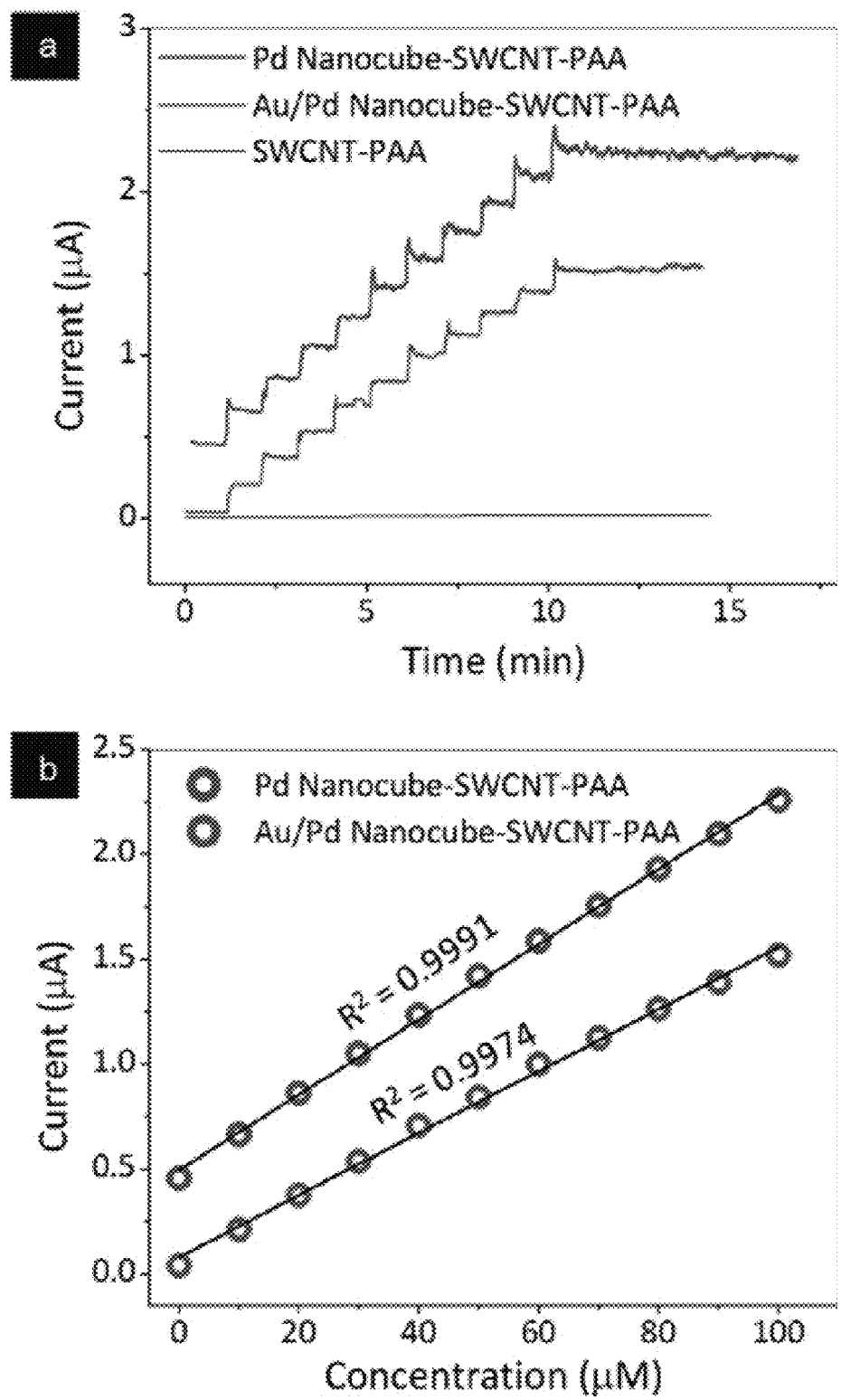
FIGS. 4a and 4b are graphic representations of the electrical response of a biosensor according to one embodiment of the present invention.

In comparison to the bare SWCNT electrode, both of the nanocube-augmented electrodes exhibit increases in current associated with each successive addition of $H_2O_2$ and demonstrate linear regressions for $H_2O_2$ oxidation (FIG. 4). The sensitivity of the Au/Pd nanocube-SWCNT electrode (370

μA mM$^{-1}$ cm$^{-2}$) is slightly lower than the sensitivity of the Pd nanocube-SWCNT electrode (448 μA mM$^{-1}$ cm$^{-2}$). This decrease in sensitivity confirms the enlargement of nanocube size by Au electrodeposition, which decreases the ratio of surface atoms with free valences to the cluster of total atoms, thus reducing sensitivity. The SWCNTs of the bare SWCNT electrode are not electrically contacted to the underlying Ti conduction layer (See FIG. 1a) and therefore show little amperometric response to $H_2O_2$.

Figure 5:
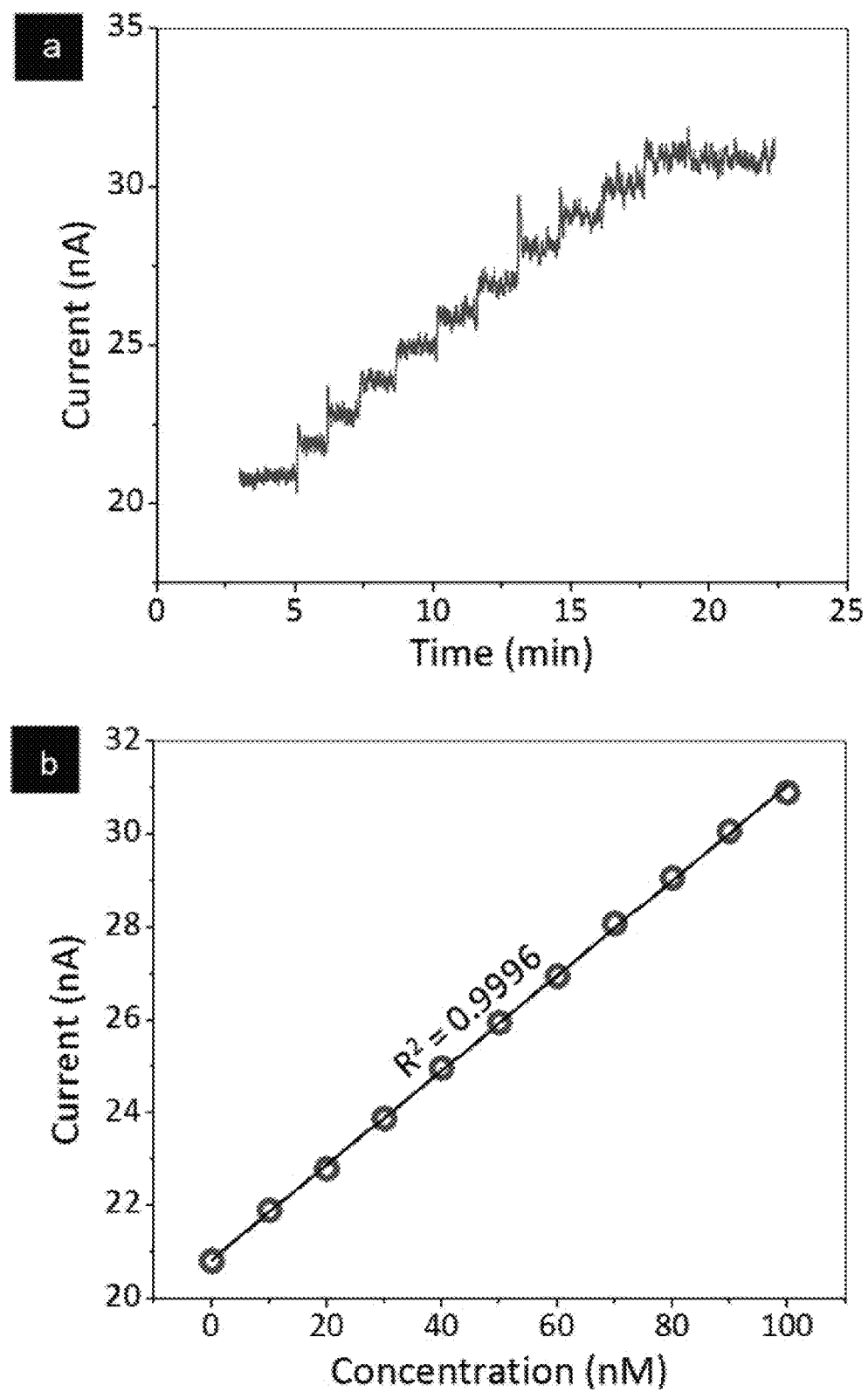
FIGS. 5a and 5b are graphical representations of the electrical characteristics of a biosensor according to one embodiment of the present invention.

To further increase sensitivity, the Au/Pd nanocube-SWCNT biosensor 20 was electrochemically treated with 0.1 M $H_2SO_4$ at a potential scan that is cycled between 0 and 1.5 V with a scan rate of 100 mV/s for 25 cycles. The process is subsequently repeated with 0.1 M NaOH. After these electrochemical pretreatments, the Au/Pd nanocube-SWCNT electrode consistently detects $H_2O_2$ concentrations as low as 10 nM with a sensitivity of 2.6 mA mM$^{-1}$ cm$^{-2}$ and a calculated detection limit of 2.3 nM (S/N=3) (FIG. 5). This $H_2O_2$ detection limit is 1-3 orders of magnitude lower than comparable SWCNT and colloidal Au nanoparticle-based amperometric biosensors. This increased electrocatalytic activity toward the oxidation of $H_2O_2$ is caused by the increase of defect sites and oxygenated species at the SWCNT sidewalls due to the 0.1 M $H_2SO_4$ and 0.1 M NaOH treatments, respectively. Increased defect sites and surface oxide species can enhance the electron transport through the otherwise relatively inert SWCNT sidewalls.

FIGS. 5a and 5b are graphs pertaining to amperometric hydrogen peroxide detection from a Au/Pd nanocube-SWCNT biosensor 20 that has been pretreated in $H_2SO_4$ and NaOH. (a) Response in 20 mL of PBS (pH 7.4) with the biosensor polarized at a working potential of 0.5 V using a three electrode potentiostat. Successive additions of $H_2O_2$ aliquots increased the peroxide concentration by 10 nM. The resulting data was processed and plotted (b) as a scatter plot (current vs concentration) with linear regression analysis.

Enzymatic glucose biosensors have been analyzed more than any other enzyme based biosensor because of their role in blood glucose monitoring in diabetic patients. GOx-based amperometric biosensors 20 according to one embodiment of the present invention measure the glucose concentration by the electrocatalytic detection of redox reaction product 10 (hydrogen peroxide) produced during the GOx/glucose reaction. The chemical reactions for this enzymatic breakdown of a substance 10 such as glucose via GOx along with the subsequent oxidation of hydrogen peroxide are as follows:

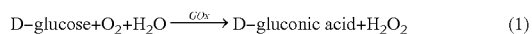

$$\text{D-glucose} + O_2 + H_2O \xrightarrow{GOx} \text{D-gluconic acid} + H_2O_2 \quad (1)$$

$$H_2O_2 \rightarrow 2H^+ + O_2 + 2e^- \quad (2)$$

Figure 6:
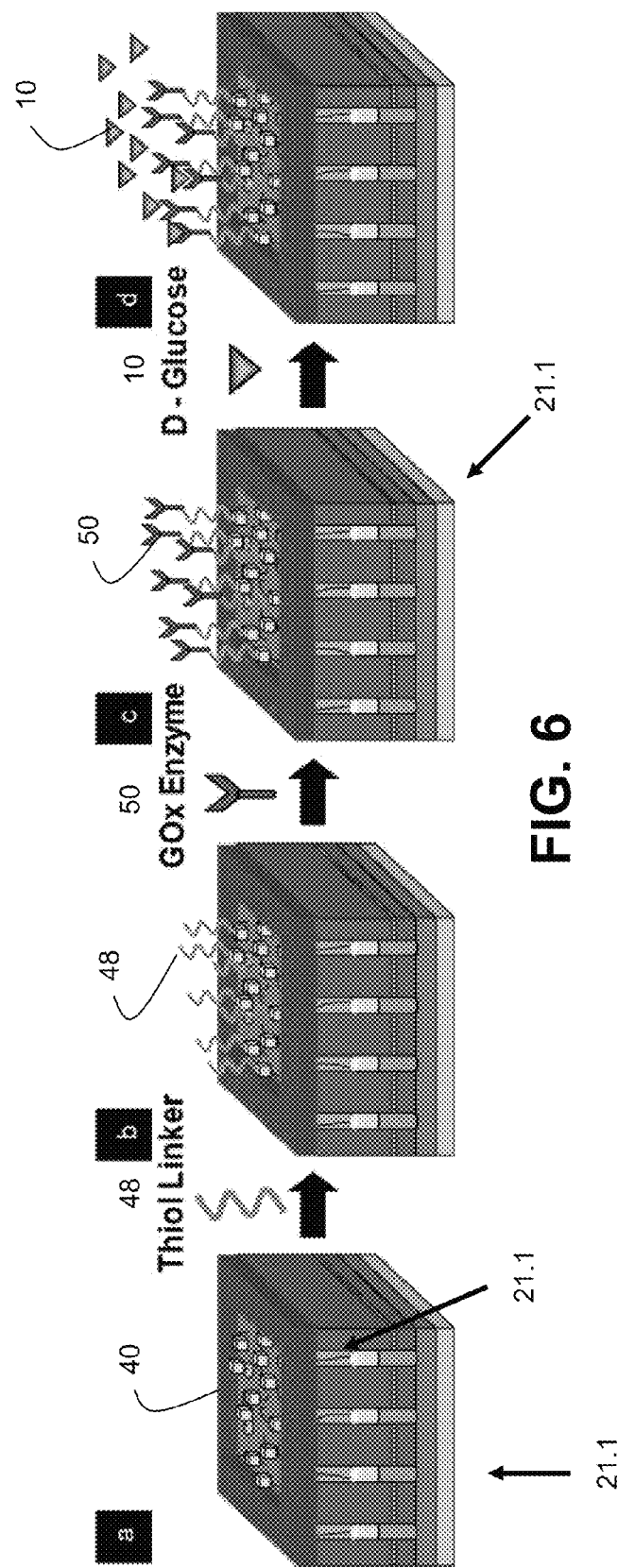
FIGS. 6a, 6b, 6c, and 6d are schematic representations of a process for fabricating a biosensor according to one embodiment of the present invention.

To prepare samples for glucose sensing, GOx molecules are coupled to the Au/Pd nanocubes by a simple two-step biofunctionalization procedure illustrated in FIG. 6. FIGS. 6a, 6b, 6c, and 6d are tilted cross-sectional schematics illustrating electrode bioconjugation process steps: (a) a lithographically defined Au/Pd nanocube-SWCNT biosensor, (b) thiol covalent linking of dithiobis (succinimidyl undecanoate) to Au/Pd nanocubes, (c) covalent linking of GOx enzyme to thiol linker, and (d) attachment of D-glucose molecules to selective GOx sites.

First, the Au/Pd nanocube-SWCNT electrodes 21.1i are incubated for 10 h in a solution including a thiol linker 48 solution [dithiobis (succinimidyl undecanoate)] dissolved in tetrahydrofuran (THF) (1 mg/mL), followed by rinsing with ultrapure water. During this incubation, the thiol linker molecules 48 selectively attach to the Au surface on the nanocubes 40. The thiol linker-bound chip is subsequently incubated with GOx [1 mg/ml in PBS (pH 7.4)] for 5 hours. This incubation causes the GOx enzymes to attach to the thiol linkers on the nanocubes. The GOx functionalized chip is triple-rinsed with ultrapure water before amperometric glucose sensing. The addition of the enzymes onto the electrodes 21.1 results in a biosensor 20.

Figure 7:
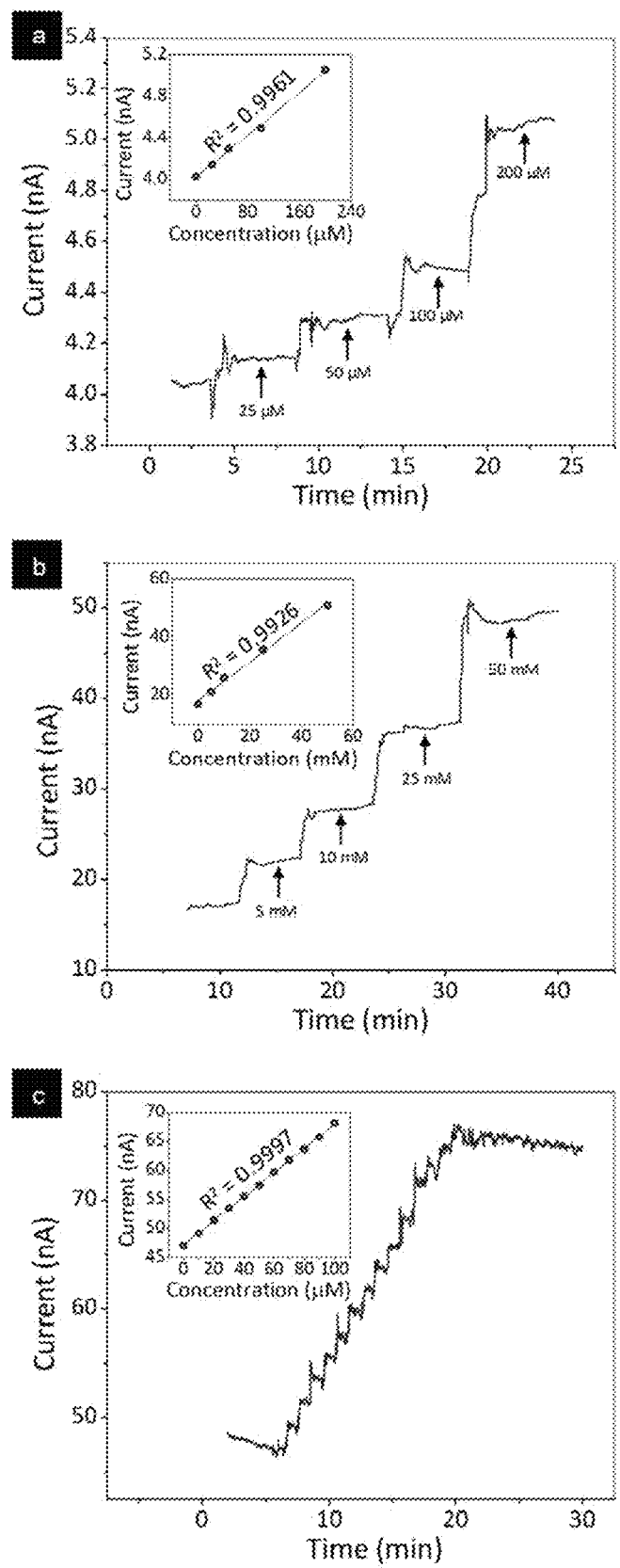
FIGS. 7a, 7b, and 7c are graphical representations of the electrical characteristics according to one embodiment of the present invention.

Glucose sensing was accomplished with the same electroanalytical procedures used in the control experiments with hydrogen peroxide. The $H_2O_2$ generated from the enzymatic reaction of GOx and D-glucose is oxidized at the conductive SWCNTs and Au/Pd nanocube surfaces, producing a redox current that is proportional to the glucose concentration. The Au/Pd nanocube-SWCNT biosensor with a lithographically defined area of 0.04 cm2 exhibits a highly linear glucose sensing range extending from 10 μM to 50 mM with a response time ~6 s (FIG. 7a, b). After the electrochemical treatment mentioned heretofore, 10 μM glucose concentration increments were successively detected at a sensitivity of 5.2 μA mM$^{-1}$ cm$^{-2}$ and an estimated glucose detection limit of 1.3 μM (S/N=3) (FIG. 7c). This wide linear range and low detection limit indicates that the Au/Pd nanocube surface has a high capacity to immobilize active GOx.

FIGS. 7a, 7b, and 7c are graphs pertaining to electrochemically coupled glucose biosensor calibration experiment in 20 mL of PBS (pH 7.4). The biosensor 20 is polarized to a working potential of 0.5 V and additions of glucose 10 were added sequentially. Different concentration increases are used in the three representative calibrations including labeled concentration increases from (a) 25-200 uM increments and (b) 10-50 mM increments. (c) A biosensor that has been pretreated with H2SO4 and NaOH is calibrated by adding glucose concentrations in increments of 10 uM. The insets show the linear regression analysis of the current vs concentration profiles for each of the experiments.

As summarized in Table 1, the Au/Pd nanocube-SWCNT electrode outperforms comparable amperometric glucose biosensors based on AuNPs aligned SWCNT arrays Au-MWCNT arrays, and Au nanowires (AuNWs) in terms of detection limit, linear range, and response time. In particular, the detection limit of the Au/Pd nanocube-SWCNT biosensor is lower and the linear range is higher than similar CNT and AuNP-based glucose biosensors (Table 1). This performance enhancement can be attributed to a number of factors, including the controlled highly sensitive surface area, the low electrical resistance pathway at the nanocube-SWCNT interface, and the selective enzyme adhesion, activity, and electron transfer that occurs between the enzyme/Au/Pd nanocube interfaces. In comparison to other known methods, various embodiments of the present invention utilize adsorption techniques and covalent linking to SWCNTs and AuNPs to immobilize enzymes onto the electrode interface.

An additional aspect of the Au/Pd nanocube-SWCNT biosensor is the ability to control the size and density of the nanocubes that decorate the SWCNTs. Optimizing the nanocube size and density for enzyme loading can produce a maximized amperometric output signal. Other reported SWCNT-Au nanoparticle electrodes rely on nanoparticle adsorption or chemical linking techniques in which nanoparticle size, density, and SWCNT/nanoparticle adhesion vary widely. Another aspect is the small size and high surface area of the Au/Pd nanocubes, which enhances the performance of the biosensor in the peroxide oxidation process. The low detection limit and linear range extending over 4 orders of magnitude implies that the immobilized GOx is highly active, indicating that the electrode provides a microenvironment suitable for the tertiary structure of the enzyme while providing a low resistance pathway for glucose diffusion and subsequent oxidation of peroxide close to the electrochemical gold surface.

Au/Pd 40 nanocubes were grown at the defect sites of templated SWCNT 30 networks through an electrodeposition process. By altering the electrodeposition current, time, and metal salt concentration the size and morphology of the Au/Pd nanocubes could be controlled. The in situ fabrication of Au/Pd nanocubes on as-grown SWCNTs eliminates the need for complicated sorting, washing, and post processing of some SWCNT-electrode immobilization schemes. Fluorescently labeled streptavidin was successfully bound to thiolated biotin ligands that were selectively immobilized on the Au/Pd nanocube surfaces, demonstrating the nanocubes ability to be biofunctionalized with covalent thiol linking schemes. The nanocube-augmented SWCNT biosensor effectively sensed successive increases of 10 nM $H_2O_2$ with a calculated current density of 2.6 mA $mM^{-1}$ $cm^{-2}$. This high sensitivity toward $H_2O_2$ makes the biosensor a good platform for oxidase-based biosensing.

The electrode was demonstrated as a glucose biosensor by immobilizing GOx on the surface of the nanocubes via thiol linking. Amperometric glucose sensing revealed that the nanocube-augmented SWCNTs outperformed similar SWCNT and metallic nanoparticle-based biosensors in terms of glucose detection limit, linear range, and response time. These results, combined with the biocompatibility of Au/Pd nanocubes, make this biosensor a candidate for a wide range of biofunctionalization schemes and biomarker detection strategies. The performance of this approach is sufficient for adaptation to a microbiosensor format that could be used as a tool for biomedical research in single-cell biosensing applications. Further description of the aforementioned apparatus and methods are provided in the following paragraphs.

PBS (0.1 M pH 7.4) was obtained from Invitrogen Corporation. Invitrogen. Dithiobis (succinimidyl undecanoate) (10 mg, stored at 4° C.) was obtained from Dojindo Molecular Technologies, Inc. GOx (*Aspergillus niger* lyophilized powder, 100000-250000 units/g, stored at 20° C.), $H_2O_2$ (30% (w/w) in $H_2O$, stored at 4° C.), tetrahydorfuran (THF) (anhydrous>99.9% inhibitor free), palladium chloride (99.999% purity, 500 mg), and gold(III) chloride hydrate (99.999% purity, 500 mg) were obtained from Sigma Aldrich. Biotinylated PEG alkanethiol (25 mg, stored at 4° C.) was obtained from Senso Path Technologies. Fluorescently labeled streptavidin (21832 Streptavidin Dylight Alexa 488) and biotin linker (21341 EZ-Link Biotin HPDP) were obtained from Pierce Chemical Co. Oxalic acid dihydrate (ACS, 250 mg) was obtained from Alfa Aesar. Hydrochloric acid (HCL, 6 lb) which was added to the 2 mM PdCl2 bath was obtained from J. T. Baker.

In one embodiment, the porous anodic alumina template was synthesized from a metal film stack including consecutive metal layers of Ti (100 nm), Al (100 nm), Fe (1 nm), and Al (400 nm) that were thermally evaporated on an oxidized silicon wafer [P<100>Si (375 nm), $SiO_2$ (100 nm)] via a thermal evaporator (Veeco 7760). The underlying Ti metal layer serves two roles: (1) supplies the bottom electrode electrical contact and (2) acts as an adhesion layer for subsequent metal deposition. The Fe layer embedded within the Al metal layers supplies the catalytic nucleation point for SWCNTs. The metalized substrate was immersed in 0.3 M oxalic acid bath held at 5° C. and biased with 40 V versus a Pt gauze auxiliary electrode. This anodization process transforms the Al metal layers into the dielectric $Al_2O_3$, forming semiordered pores (20-30 nm in diameter) through the Al/Fe/Al metal layers known as porous anodic alumina (PAA) or anodic aluminum oxide (AAO). A portion of the substrate was not anodized, leaving an electrically conductive contact pad composed of the evaporated metals for subsequent electrodeposition and amperometric sensing.

Electrically addressable individual SWCNTs were grown from an Fe layer embedded in the pores of the PAA through a microwave plasma enhanced chemical vapor deposition (MPCVD) reactor (SEKI AX5200S). The anodized substrate was placed on a 5.1 cm diameter molybdenum puck and heated in a hydrogen ambient to 900° C. by a 3.5 kW radio frequency power supply. Once the sample reached 900° C., a 5 kW ASTeX AX2100 microwave generator was powered to create an unbiased 300 W hydrogen plasma over the substrate. This hydrogen plasma serves a dual purpose, (1) it penetrates the oxide barrier at the base of the PAA pores and (2) it decomposes methane, which acts as a precursor for SWCNT growth. After hydrogen plasma formation, methane was introduced into the MPCVD for 10 min to achieve SWCNT growth. The SWCNTs extend vertically from the pores of the PAA eventually resting horizontally on the surface of the PAA itself and vary in length from 3-10 μm (See FIG. 1a).

Decoration of the SWCNTs with Pd nanoparticles was performed by a BASi Epsilon three electrode cell stand. Pt gauze acted as the auxiliary electrode, an Ag/AgCl wire as the reference electrode, and the SWNCT/PAA substrate as the working electrode. Pd was galvanostatically electrodeposited on the SWCNT-PAA structure by applying 500 ms pulses of 2 mA/cm² current between the auxiliary and working electrode for 250 cycles in a 2 mMPdCl₂ bath. Pulse currents allow for the double layer to dissipate between cycles allowing for consistent and controlled Pd deposition in the pores and defect sites of the SWCNT-PAA templated structure. After Pd electrodeposition, the samples were rinsed in DI water and allowed to air-dry. The Pd electrodeposition serves two roles, (a) supplies the back contact to the SWCNTs by partially filling the pores of the PAA connecting the Ti bottom layer and Fe layer and (b) forms well-defined Pd nanocubes at SWCNT defect sites (See FIG. 1b).

Yet other embodiments of the present invention contemplate a fabrication range for a current pulse electrodeposition technique using a current pulse between about 2 and about 6 mA/cm^2 at a pulse time of about 500 ms. Electrodepositions at higher current pulses will lead to faster deposition time and slight to significant changes in the crystalline structure formation (i.e morphology) of said deposited nanoparticles. Between about 100 to about 800 pulses are used per biosensor depending on the desired size (25 nm to 500 nm) of the nanoparticle. Typically the concentrations of the Pd, Au, and Pt salt concentrations will very between about 2 and about 15 mmol/L.

Some embodiments of the present invention include SWCNTs that are further decorated with Au through the use of the same BASi Epsilon cell stand and three-electrode setup. The electrode was placed in a 15 mM HAuCl4 bath and biased with 0.65 V versus a Pt gauze auxiliary electrode for 10 s. Constant voltage electrodeposition creates a diffusion limited Au deposition so Au deposition occurs onto existing Pd and not on bare SWCNTs (See FIG. 1c). The Au thickness on the PD was varied by adjusting the electrodeposition time, bias, and metal salt concentration. Although the use of Au, Pd, and Pt are shown and described herein, other embodiments of the present invention also includes the deposition of layers and the formation of nanoparticles from silver (Ag), copper (Cu), and nickel (Ni).

The surface area of the Au/Pd nanocube-SWCNT electrode was controlled by photolithography. After electrochemical pretreatment the electrode was solvent cleaned with acetone and methanol and dried under a gentle stream of N2 to clean and prepare the samples for photolithography. Various areas were lithographically defined (5 mm×5 mm, 3 mm×3 mm, 2.5 mm×2.5 mm, 2 mm×2 mm, 0.5 mm×0.5 mm) for optimal amperometric sensitivity toward hydrogen peroxide and glucose sensing. A film of $Al_2O_3$ of thickness of 400 nm was subsequently deposited on each sample via a Leybold e-beam evaporator. A subsequent 1 h acetone soak was used to lift off the remaining PR, leaving a well-defined rectangular area of SWCNT Pd/Au surrounded by an oxide dielectric, $Al_2O_3$.

The biosensor is soaked in biotinylated PEG alkanethiol solution (0.20 mg/mL in ultrapure water) for 2 h, followed by rinsing with ultrapure water and drying under a stream of nitrogen gas. Next, the biosensor is exposed to 40 μL of fluorescently labeled streptavidin solution (Alexa-488 coupled streptavidin) for 10 min. After this incubation period, the biosensor is rinsed thrice with PBS and once with ultrapure water to remove buffer salts, followed by drying with nitrogen gas.

The biosensor was placed in 1 mL of THF that includes 1 mg of dissolved dithiobis (succinimidyl undecanoate) for approximately 10 h. The electrodes are then double rinsed with PBS (0.1 M, pH 7.4, Sigma Aldrich) and placed in a GOx solution containing 1 mg of GOx enzyme (lyophilized powder, 100000-250000 units/g, Sigma Aldrich) for every 1 mL of PBS for 5 hours. Electrodes were stored at 4° C. until electrochemical testing.

Amperometric sensing of glucose and $H_2O_2$ was performed on a BASi Epsilon three-electrode cell stand. Pt gauze acted as the auxiliary electrode, Ag/AgCl as the reference electrode, and the Au/Pd nanocube-SWCNT biosensor as the working electrode. During electrochemical measurements electrons travel from the Au/Pd-SWCNT/solution interface and through the SWCNTs to the Pd nanowires that are electrically connected to the Ti layer. The Ti layer, in turn, forms the metal underlayer of the electrically conductive contact pad of the Au/Pd nanocube-SWCNT biosensor and accordingly permits electron transfer to the cell stand. All amperometric measurements were acquired in PBS (0.1 M pH 7.4) at an overvoltage of 0.5 V.

Both optical and fluorescence images were acquired on a E1000 upright microscope (Nikon, Tokyo, Japan), using a 40×0.75 NA Plan Fluor lens (Nikon), with a Retiga Exi CCD camera (QImaging, Surrey, BC, Canada). Fluorescence images were acquired using the FITC cube and a mercury arc lamp as the light source. Optical images (reflected light images) were acquired using a beamsplitter cube and a halogen lamp as the light source. All FESEM micrographs were obtained from a Hitachi S-4800.

SECOND EXAMPLE

A metal film stack consisting of consecutive metal layers a conductive layer 124 of Ti (100 nm) and Al (400 nm) were thermally evaporated on an oxidized silicon wafer 222 [P <100> Si (375 nm), $SiO_2$ (100 nm)] via a thermal evaporator (Veeco 7760). The underlying Ti metal layer serves two roles: (1) supplies the bottom electrode electrical contact and (2) acts as an adhesion layer for subsequent metal deposition. The metalized substrate 222 was immersed in 0.3 M oxalic acid bath held at 5° C. and biased with 40 V versus a Pt gauze auxiliary electrode. This anodization process transforms the Al metal layers into the dielectric layer 226 ($Al_2O_2$), forming semi-ordered pores 226.3 (20-30 nm in diameter) known as porous anodic alumina (PAA) or anodic aluminum oxide (AAO). A portion of the substrate was not anodized, leaving an electrically conductive contact pad composed of the evaporated metals for subsequent electrodeposition and amperometric sensing.

To open the dielectric alumina barrier within the pore bottoms of the PAA and expose the Ti under layer, the anodized substrate was exposed to a hydrogen plasma within a microwave plasma enhanced chemical vapor deposition (MPCVD) reactor (SEKI AX5200S). Au was galvanostatically electrodeposited on the exposed Ti under layer of the PAA substrate by applying 500 ms pulses of 5 mA/$cm^2$ current between the auxiliary and working electrode for 150 cycles in a 25 mM $HAuCl_4$ bath. Pulse currents allow for the double layer to dissipate between cycles allowing for consistent and controlled Au deposition in the pores of the PAA. The Au electrodeposition was continued until the pores of the PAA were overfilled and a gold sheen was visible on the surface of the substrate. The gold nanorods 230 are solid structures of crystalline gold. They are single crystal structures and similar to the cubic Pd nanocubes. Single crystal structures have no grain boundaries and therefore good charge transport properties.

Figure 19A:
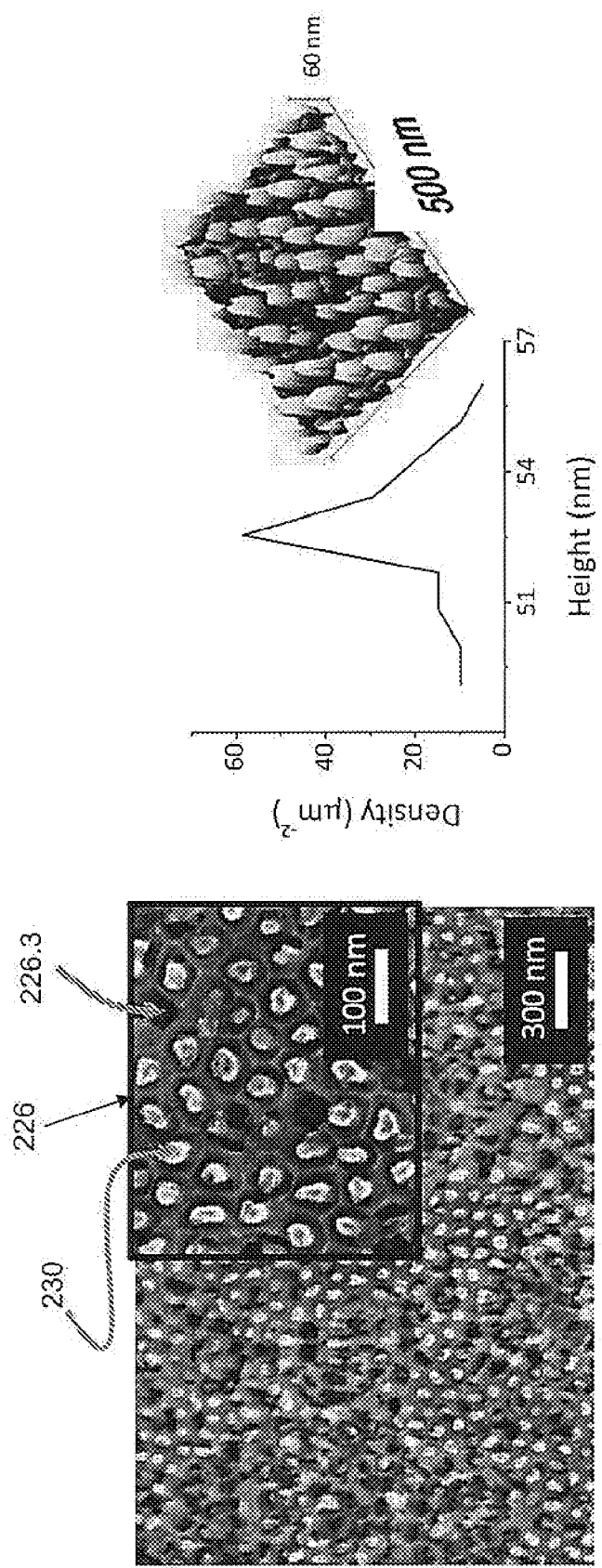

FIGS. 19a, 19b, and 19c show FESEM images of Au nanorod 230 electrodes extending from the etched back PAA template with corresponding mean height distribution plots and 3D color enhanced images. The distinctly sized Au nanorod structures were created by etching back the PAA in a chromic acid bath for (a) 6 min; (b) 12 min; and (c) 18 min. A 6 min Ar reactive ion etch (RIE) process with the Panasonic E620 Etcher milled away the top layer of gold on the PAA, exposing the tips of the gold nanorods. Further selective etching of the PAA template via a chromic acid bath held at 65° C. for 6 min, 12 min, and 18 min exposed gold nanorods approximately 52 nm, 113 nm, and 162 nm in length respectively.

The surface area of the Au nanorod biosensor was controlled by photolithography. Photoresist (AZ 1518) was spin-coated on the electrode, exposed to UV light (power 23 mV for 9 seconds) through a masking step, and then developed. A rectangular window of photoresist was left on the electrode. The final layer of alumina was deposited on the electrode and then the electrode was soaked in acetone overnight. This acetone soak "lifted-off" the remaining PR on the electrode and thus the alumina layer on top of the PR was removed from the electrode exposing electrochemically active region of the Au nanorod sensor. A 0.4 mm by 0.4 mm lithographically defined area was defined on each Au nanorod electrode to analyze the electrochemical response of the distinctly sized gold nanorod electrodes. The window (electrochemically active region of the electrode) size can be changed to increase or decrease electrode sensitivity. The FESEM images were taken within that open window area and therefore the top 400 nm thick alumina layer is not visible in the images. A film of $Al_2O_3$ of thickness of 400 nm was deposited on each sample via a Leybold e-beam evaporator.

Electrochemical biosensors 220 can involve the exchange of an electron or electrons between a species in solution and an electrode surface. The magnitude and direction of this electron transfer is understood by analysis of the Nernst equation:

$$E = E° + \frac{RT}{(nF)} \ln\left(\frac{[Ox]}{[Red]}\right) \quad (3)$$

where R is the gas constant (8.314 $mol^{-1} K^{-1}$), T is absolute temperature ln Kelvin, n is the number of electrons transferred, F is Faraday's constant ($9.6485309 \times 10^4$ C mol$^{-1}$), and Ox and Red are the respective concentrations of oxidized and reduced species. The formal potential, $E^0$, is the measured potential of the electrochemical half cell versus the Normal Hydrogen Electrode (NHE) and is a function of the activities of the Ox and Red species (Equation 4).

$$Ox + ne^- = Red \quad (4)$$

Figure 21:
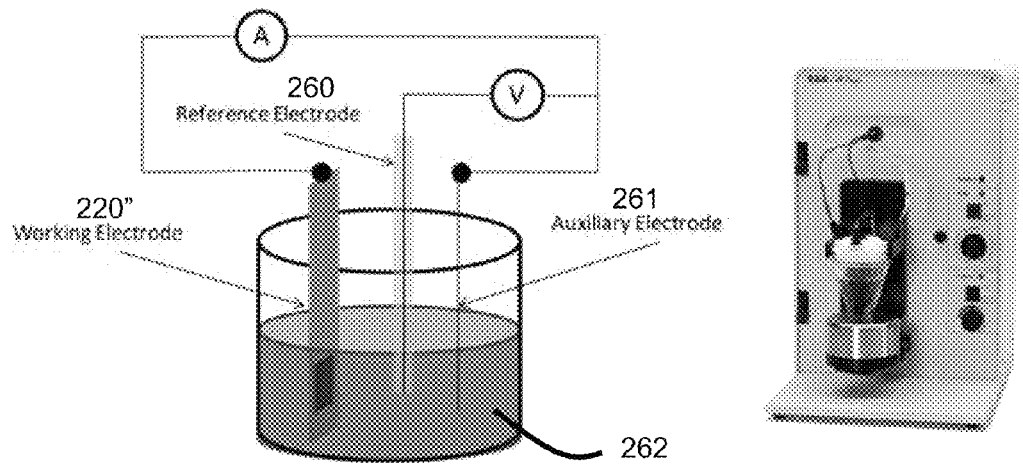
FIG. 21 shows schematic and photographic representations of a method according to one embodiment of the present invention.

In amperometric sensing, a bias is applied between the working and auxiliary electrodes, shifting Equation (4) from equilibrium and subsequently forcing electron transfer at the working electrode/solution interface. This electron transfer is monitored as a current, which is directly proportional to the concentration of analyte being oxidized or reduced. A 3-electrode potentiostat (BASi Epsilon Cell Stand), which includes a working electrode 220" (a biosensor 220 configured as an electrode), a reference electrode 260 and an auxiliary electrode 261 is utilized for subsequent amperometric sensing measurements. FIG. 21 shows schematic and photographic representation of a 3-electrode electrochemical set-up for amperometric sensing including the working electrode as the Au nanorod, a Ag/AgCl wire as the reference electrode 260 and a Pt wire as the auxiliary electrode 261 including an image of BASi Epsilon Cell Stand upon which the amperometric sensing is performed. The biosensor 220 serves as the working electrode 220", a platinum wire as the auxiliary electrode, and Ag/AgCl as the reference electrode.

Figure 22:
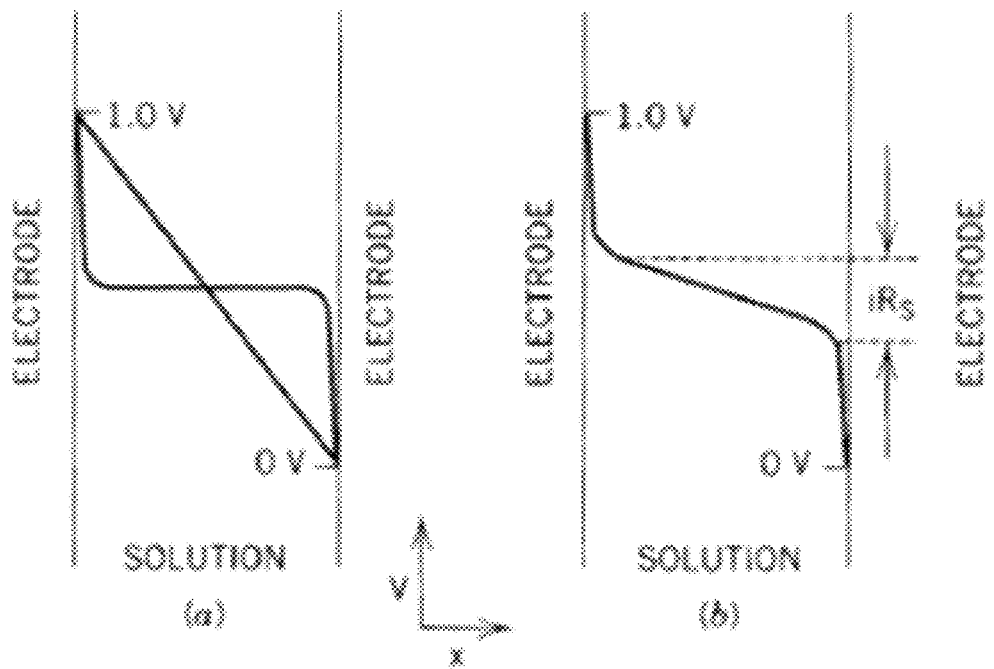
FIGS. 22a and 22b are graphical representations of the potential drop between two electrodes.

Amperometric sensing experiments are carried out in phosphate buffer solution (PBS) having a ph of 7.4. The PBS 262 serves two roles: (1) it supplies a controlled pH environment for optimal enzyme activity, and (2) it provides an ionic medium that promotes the formation of an electrochemical double layer around the working and auxiliary electrodes respectively. FIGS. 22a and 22b are schematic diagrams of the potential drop between two electrodes. The potential drop is linear (a) in the absence of electrolyte. When electrolyte 262 is added (b) a double layer (of nanometer-range thickness) forms at each electrode, resulting in a relatively small potential ($iR_s$) throughout the bulk solution, where (i) is the current flowing through the solution and $R_s$ is the resistance of the solution.

The formation of this double layer is helpful for electrochemical-based biosensors. The electrochemical double layer includes a build-up of ions from the electrolyte medium (PBS) near the working and auxiliary electrode surfaces due to electrostatic forces. This build-up of ions causes most of the potential drop to occur within a small nanometer width boundary layer between the working electrode/solution and auxiliary electrode/solution interfaces. This electrochemical double layer shields the bulk solution from the bias applied to the working electrode and auxiliary electrode during electrochemical experiments, thus maintaining the stoichiometry of the bulk solution by preventing migration of electrochemically generated charged species within the bulk solution towards the working or auxiliary electrodes.

Figure 20:
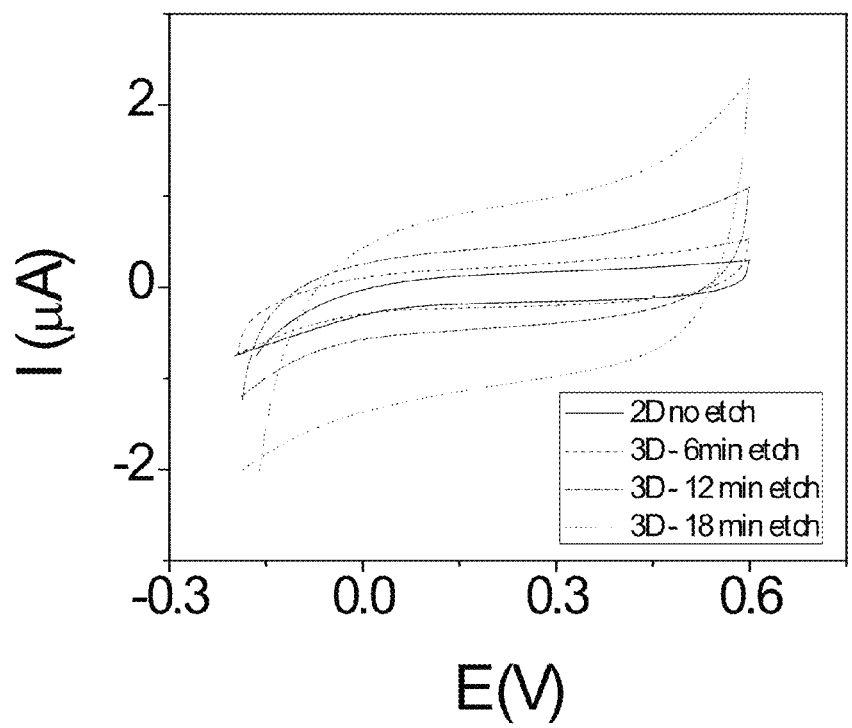
FIG. 20 is a graphical representation of the electrical characteristics of a sensor according to one embodiment of the present invention.

Cyclic voltammetry scans of the distinctly sized Au nanorod biosensors characterize the electrochemical response of the Au nanorod biosenors. FIG. 20 shows cyclic voltammetry (CV) scans cycled between −200 and +400 mV at a rate of 100 mV/s within a 1 mM $KNO_3$ solution for 2D and 3D Au nanorod electrodes with PAA chromic acid etch back times of 0, 6, 12, and 18 minutes, respectively.

From the CV scans presented in FIG. 20 and the peak capacitive currents of the distinctly sized Au nanorod electrodes presented in Table 1, the increase in capacitive current is found to be approximately proportionally to the increase in nanorod length.

TABLE 1

| | Etching Time | | | |
|---|---|---|---|---|
| | 0 min | 6 min | 12 min | 18 min |
| Peak capacitative current (μA) | 0.29 | 0.53 | 1.10 | 2.29 |
| Increase in capacitative current | | 1.8 times | 3.7 times | 7.8 times |

This proportionality is further corroborated according to Equation (5) where capacitative current is proportional to the electrochemically active surface area of the biosensor.

$$I_c = kAv \quad (5)$$

where:
v = scan rate (100 mV/s)
A = effective electrochemically active surface area
k = constant = $\epsilon_r \epsilon_0 d$
  where:
    $\epsilon_r$ = relative static permittivity
    $\epsilon_0$ = permittivity of free space
    d = distance between working and counter electrodes These results verify the electrochemical capability of the in-situ synthesized Au nanorod biosensor 220. Furthermore the proven biocompatibility and biofunctionalization capability of gold make the Au nanorod biosensor well-suited for a wide range of electrochemical biosensing applications, including the detection of glucose.

In some embodiments of the present invention the electrode can be a nanoelectrode 221 comprising a conductive material (such as gold) electrode deposited within a pore 226.3 of a porous insulating and dielectric layer 226. In such embodiments, the electrode does not include a carbon nanotube.

Electrode 221 in one embodiment is a single crystal structure of gold electrode deposited within a pore of a porous anodic alumina substrate. One end of electrode 221 is in electrical communication with other ends of electrodes on the substrate. The other end of the electrodes 221 include an electrodeposited nanoparticle 240, similar to the other nanoparticles described herein. The nanoparticles are electrodeposited on the portion of the nanoelectrode that extends out of the opened end of the pore.

Further, as described elsewhere herein, an enzyme 250 can be immobilized onto the nanoparticle. The enzyme can be immobilized onto the nanoparticle by any of the processes described herein. Further, in some embodiments, the nanoparticle is electroplated with a metal (such as gold) prior to immobilization of the enzyme. Still further, in yet other embodiments, the nanoparticle is washed in an acid bath and/or an alkali bath prior to immobilization, so as to increase the number of defect sites on the nanoparticle. In still other embodiments, the enzyme are immobilized directly on the metal nanorods.

THIRD EXAMPLE

Glucose biosensors comprised of nanomaterials such as carbon nanotubes (CNTs) and metallic nanoparticles offer electrochemical performance that produce glucose sensing by detection of products resulting from the redox reaction of a substance 110 such as glucose. Various embodiments of the present invention provide for biosensor fabrication and biofunctionalization procedures that utilize CNTs electrochemically decorated with Pt nanospheres to sense glucose amperometrically with good sensitivity.

In one embodiment, CNTs 130 are grown in situ by microwave plasma chemical vapor deposition (MPCVD) and electrochemically decorated with Pt nanoparticles 140 (examples include nanospheres and nanocubes) to form a CNT/Pt nanoparticle composite biosensor 120. CNT electrodes are immobilized with fluorescently labeled bovine serum albumin (BSA) and analyzed with fluorescence microscopy to demonstrate their biocompatibility. The enzyme glucose 150 oxidase (GOx) is immobilized on the CNT/Pt nanoparticle biosensor by a drop-coat method for amperometric glucose sensing.

Fluorescence microscopy verifies the ability of MPCVD-grown CNTs 130 to adsorb fluorescently labeled BSA, demonstrating biocompatibility prior to subsequent electrochemical biosensing experiments. The GOx-CNT/Pt nanosphere biosensor demonstrates a sensitivity towards $H_2O_2$ (7.4 $\mu A\ mM^{-1}\ cm^{-2}$) and glucose (70 $\mu A\ mM^{-1}\ cm^{-2}$), with a glucose detection limit and response time of 380 nM (S/N) and 9 seconds ($t_{90}$%) respectively.

The GOx-CNT/Pt nanosphere biosensor 120 provides nanoparticle/CNT composite biosensors with good glucose sensitivity and low detection limits. Furthermore, these biosensor fabrication and biofunctionalization schemes can be scaled for integration into commercial applications that include highly sensitive and accurate glucose sensing.

A CNT biosensor 120 according to one embodiment of the present invention is fabricated in situ from an oxidized silicon wafer 123 [P <100> Si (5 $\mu$m), $SiO_2$ (500 nm)] upon which a porous anodic alumina (PAA) template 126 is created for subsequent CNT 130 growth by a method previously reported. This PAA template is created by consecutively evaporating a thin metal film stack consisting of a conductive layer 124 such as titanium (100 nm), an electrically insulating and dielectric inner layer 126.1 such as aluminum (100 nm), a catalytic layer 125 such as Fe (1 nm), and another insulating and dielectric top layer 126.2 such as aluminum (400 nm). The metallized silicon wafer is anodized by biasing the substrate to 40 V relative to a Pt auxiliary electrode within an oxalic bath (0.3M, 5° C.). This anodization process not only forms semi-ordered pores that extend through the inner and top layers 126.1 and 126.2, respectively, and Fe layers to the underlying Ti layer, but also creates a corrosion-resistant surface that decreases the extent of chemical fouling during electrochemical biosensing. A portion of the substrate is left un-anodized, leaving an electrically addressable metal contact pad for subsequent electrochemical processing and for possible electronic integration with portable glucose monitoring systems.

CNT synthesis initiates within individual PAA pores by a microwave plasma chemical vapor deposition (MPCVD) process (SEKI AX5200S). Within the MPCVD reaction chamber the anodized substrate is heated to 900° C. under a 10 torr hydrogen ambient by a 3.5 kW radio-frequency power supply. A 300 W unbiased hydrogen plasma is subsequently formed over the substrate, and methane gas is introduced to accomplish CNT growth. The CNTs 130 grow from the Fe catalyst layer 125 embedded within the pores of the PAA and extend horizontally, 3-10 $\mu$m in length along the surface of the substrate.

Figure 8:
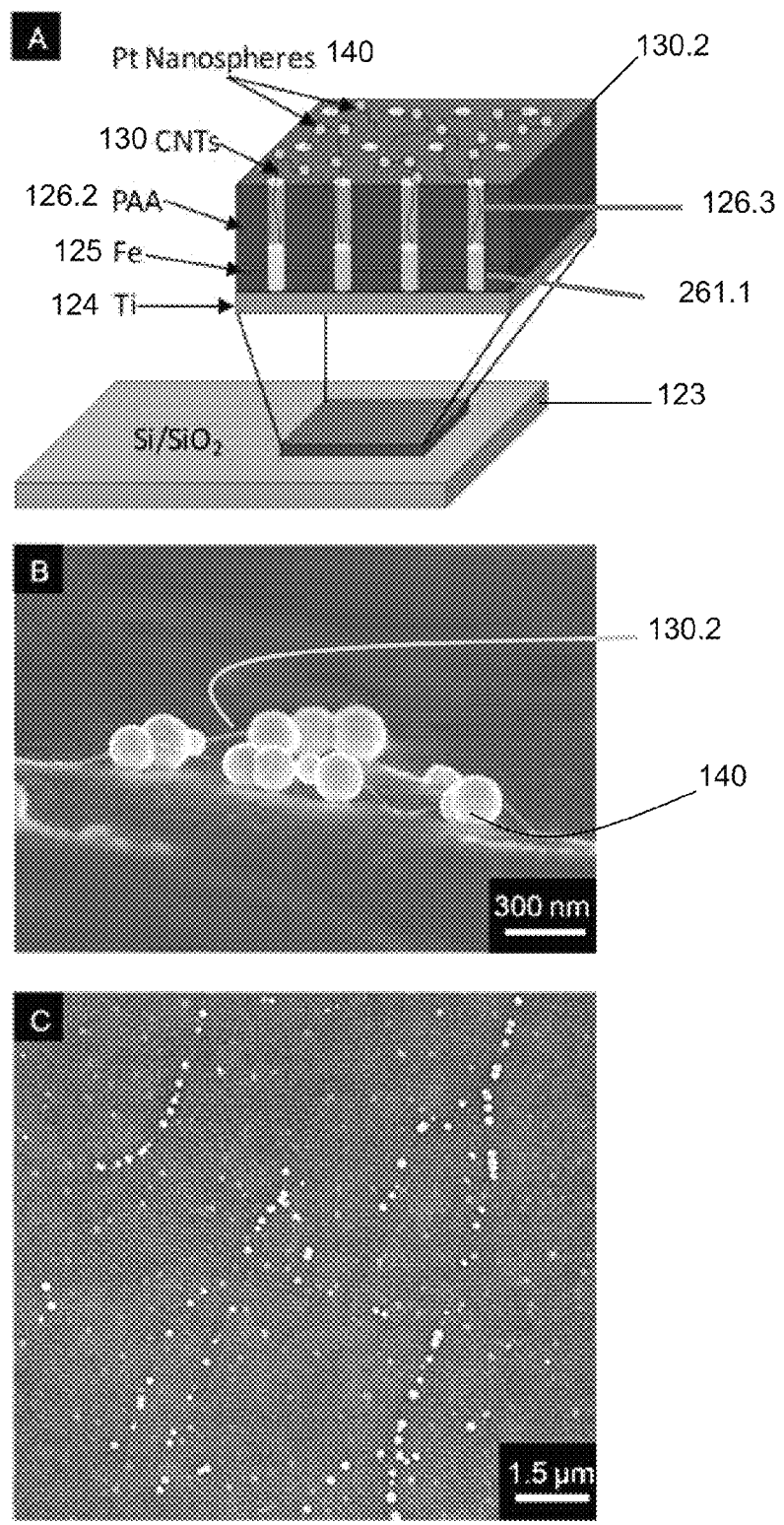
FIGS. 8a, 8b, and 8c represent schematic and photographic representations of an apparatus according to another embodiment of the present invention.

Pt from a 15 mM $H_2PtCl_6$ salt solution is subsequently electrodeposited onto the substrate through a three-electrode electrochemical set-up (BASi Epsilon Three-Electrode Cell Stand), where the CNT/PAA substrate acts as the working electrode, Pt gauze as the auxiliary electrode, and Ag/AgCl (3M NaCl) as the reference electrode. Through this electrodeposition process, Pt first partially fills the pores of the PAA—creating an electrical contact 132 (such as a Pt nanowires) between the CNTs and conducting Ti bottom layer. Once the Pt wires 132 reach the bases of the CNTs within the pores, the contacted CNTs become part of the electrode, allowing Pt nanospheres 140 (approx. 200 nm in diameter, see FIG. 8) to form concentrically at defect sites on the portions of the CNTs extending out of the pores.

FIGS. 8a, 8b, and 8c show the following: cross-sectional schematic (A) portraying the templated in-situ growth of CNTs from the PAA decorated with Pt nanospheres to form the CNT/Pt nanosphere electrode upon an oxidized silicon wafer. Field emission electron microscopy (FESEM) micrographs showing a high magnified side-view (B) and low magnified top-view (C) of Pt nanospheres 140 (~200 nm dia.) electrically wired by CNTs 130 (~1-3 nm dia).

In order to verify the biofunctionalization compatibility via physical adsorption of CNTs, a CNT electrode is first checked for auto fluorescence and then immobilized with FITC-labeled BSA (Sigma-Aldrich, Catalog #A-9771) and fluorescently analyzed again by a Nikon Labophot fluorescence microscope with a FITC filer and an Optronics 479T CCD camera. The FITC-labeled BSA is immobilized onto the CNT electrode by first immersing the electrode with PBS within an individual polystyrene well. A 5 $\mu$L solution of FITC-labeled BSA (2 mg/ml in PBS) is injected into the well and allowed to incubate at room temperature by placing the well on a rotary shaker (100 rpm for 30 minutes). The CNT electrode is then washed 3 consecutive times by injecting the well with fresh PBS and agitating it with the rotary shaker (100 rpm for 5 minutes). This rigorous washing scheme helps to minimize nonspecific binding by eliminating any unbound FITC-labeled BSA from the CNT surface. The washed CNT electrode is analyzed with fluorescence microscopy by placing the electrode into a transparent PBS filled chamber that is created by sandwiching a silicone gasket between two glass microscope slides. Adsorped FITC-labeled BSA is observed on the biofunctionalized CNT electrode via fluorescence microscopy with exposure times of 500 ms and 1 s respectively.

Using immobilization techniques similar to those employed in the foregoing fluorescently marked BSA adsorption experiments, the CNT/Pt nanosphere electrode is converted into a glucose biosensor by immobilizing the enzyme 150 glucose oxidase to the electroactive surface of the biosensor via a cross-linking matrix of bovine serum albumin (BSA) and gluteraldehyde. Glucose oxidase (GOX) solution is prepared from a 130,000 U/gm stock (Sigma Aldrich, St. Louis, Mo.) by dissolving 25 mg of GOx in 1 ml of PBS (pH 7.4). The enzyme matrix is then created by mixing GOx solution with 2.5% BSA and 2.5% gluteraldehyde. The immobilization scheme is based on covalent linking of the enzyme with the aldehyde groups of gluteraldehyde through formation of Schiff bases. BSA serves to block the excess aldehyde sites that can denature the enzyme and aids in maximizing enzyme activity. A 5 $\mu$L drop of this enzyme matrix solution (16.25 U GOx) is uniformly pipetted onto the sensor surface and allowed to air dry for 1 hour before electrochemical testing. When not in use the biosensor is stored in PBS (pH 7.4) at 4° C.

Amperometric $H_2O_2$ and glucose biosensing is carried out through a three-electrode arrangement in which the GOx-CNT/Pt nanosphere biosensor 120 acts as the working electrode 120", a Pt wire as the auxiliary electrode 161, and Ag/AgCl as the reference electrode 160. The three electrodes are immersed in a vial containing 20 ml of an electrolyte 162 such as PBS (pH 7.4), while successive concentration increases of $H_2O_2$ or D-glucose are injected into the test vial at a working potential of 350 mV. The enzymatic reaction of GOx and D-glucose produces $H_2O_2$ (See Eq. 1 and 2) which is subsequently oxidized at the electrochemically active CNT/Pt nanosphere surface—producing a measurable electrical signal.

Figure 9:
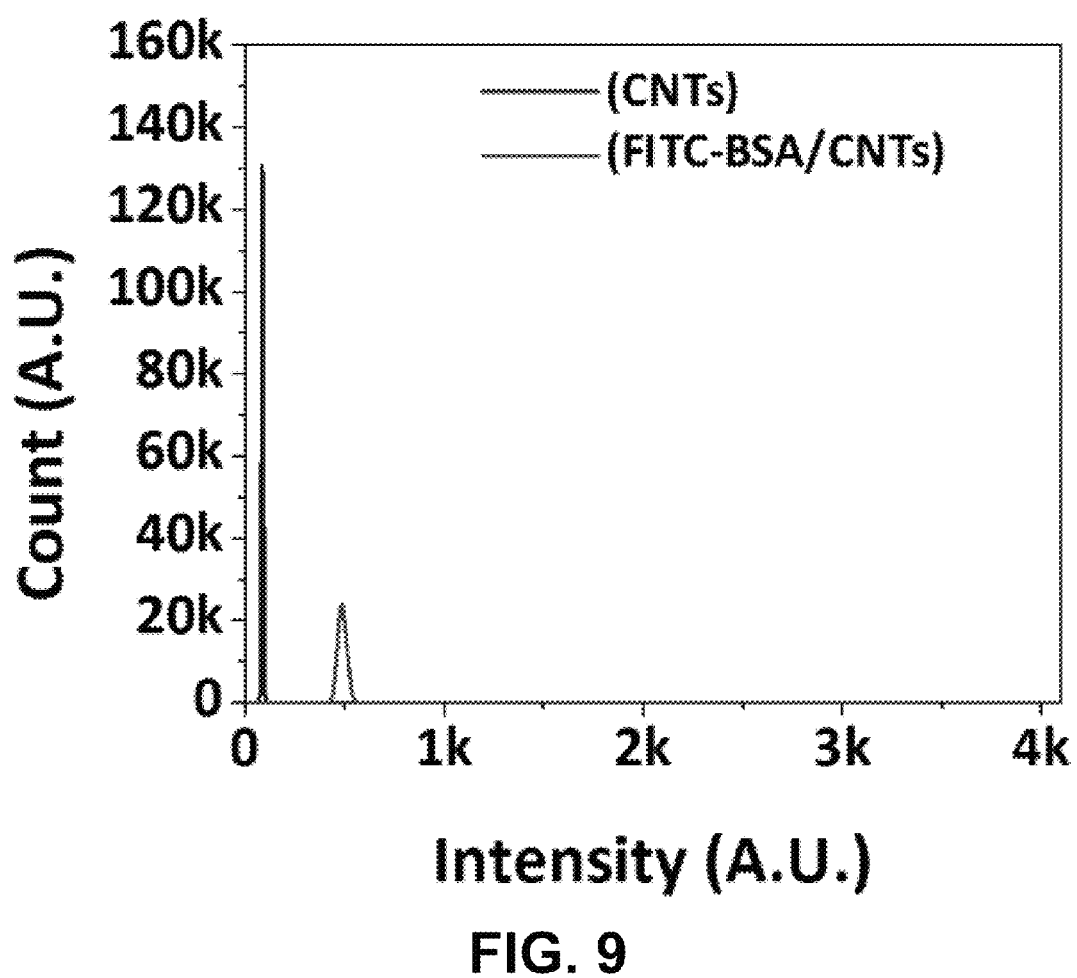
FIG. 9 show fluorescence intensity results (exposure time=1 s) for MPCVD-grown CNT electrodes with and without immobilized FITC-labeled BSA.

In order to demonstrate the biocompatibility of non-chemically altered, sorted, or washed MPCVD-grown CNT electrodes, fluorescence microscopy is employed to analyze CNT protein adsorption. Fluorescence microscopy results (see FIG. 9) reveal the relative intensity peaks of CNT electrodes with and without immobilized FITC-labeled BSA protein.

The peak with immobilized BSA protein (~0.5 k) is nearly 5 times greater in intensity then the intensity peak associated with the CNT electrode (~0.1 k). This demonstrates that MPCVD-grown CNTs that have not been chemically post-processed are capable of adsorbing active protein, an indication that these CNTs are biocompatibility for subsequent biosensing experimentation.

Figure 10:
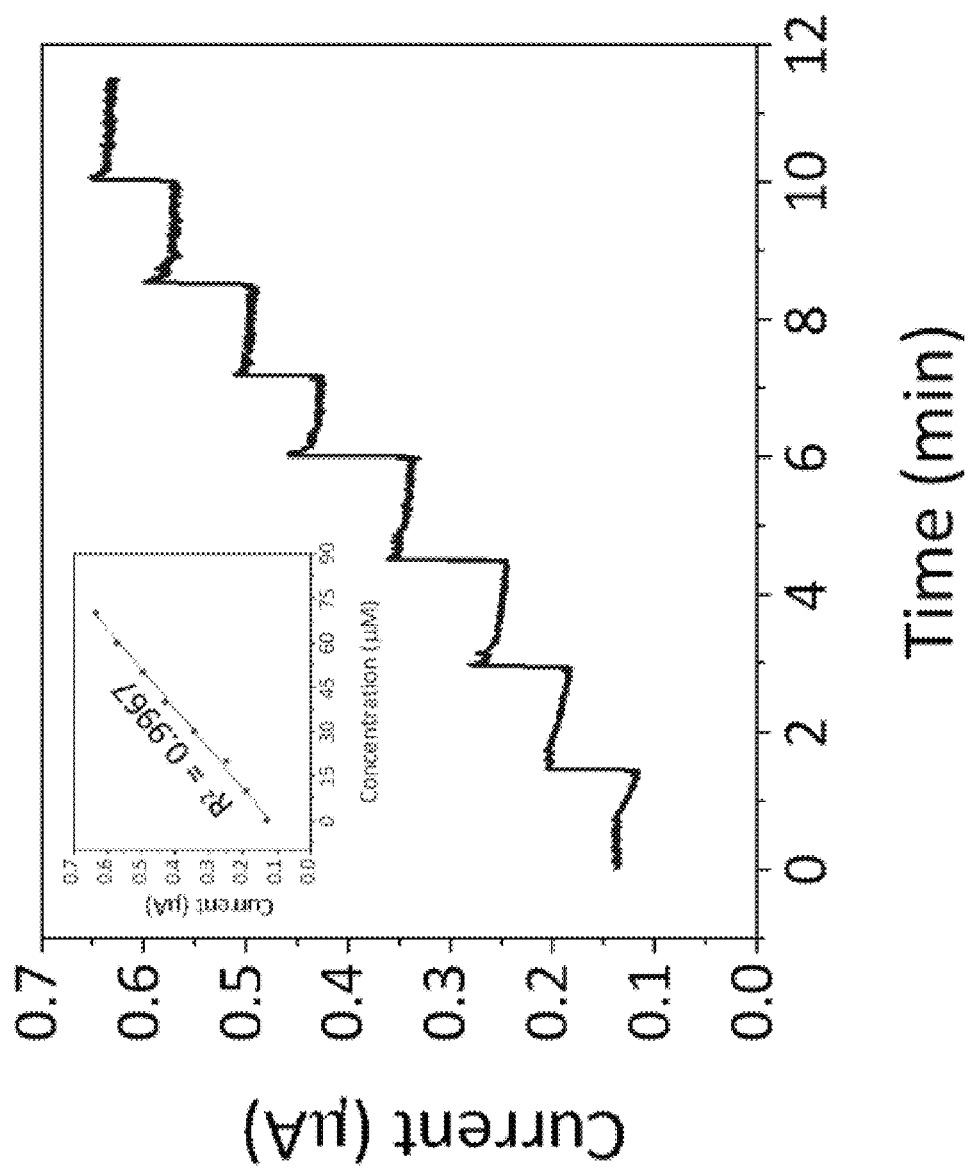
FIG. 10 shows the electrical characteristics of a biosensor according to another embodiment of the present invention.

Amperometric $H_2O_2$ testing (see FIG. 10) was performed in order to test the electroactive nature of the of the CNT/Pt nanosphere biosensor towards oxidation of reaction product 115 $H_2O_2$. The CNT/Pt nanosphere biosensor exhibits good sensitivity (7.4 $\mu A\ mM^{-1}\ cm^{-2}$) towards the oxidation of $H_2O_2$, which is the typical electron mediator between the GOx enzyme and the biosensor surface. FIG. 10 shows amperometric $H_2O_2$ sensing experiment for the CNT/Pt nanosphere biosensor. The current response to seven successive concentration increases of 10 $\mu M\ H_2O_2$ is displayed while the inset shows the linear regression analysis of the current versus concentration plot.

The GOx-CNT/Pt nanosphere composite biosensor demonstrates a linear sensing region throughout the micromolar glucose concentration range with a detection limit of 380 nM at a signal-to-noise ratio of three (S/N=3). The micromolar sensitivity of the biosensor is 70 $\mu A\ mM^{-1}\ cm^{-2}$ while the response time is 9 seconds ($t_{90\%}$). This sensitivity and detection limit of the CNT/Pt nanosphere biosensor may outperform other biosensors (see Table 1). Furthermore these comparative nanocomposite biosensors may require complex processing steps in order to immobilize CNTs and/or Pt nanoparticles onto an electrode for subsequent glucose sensing.

TABLE 1

Glucose sensing performance comparison of various biosensors.

| Biosenor Description | Sensitivity [$\mu A\ mM^{-1}\ cm^{-2}$] | Detection Limit [$\mu M$] |
| --- | --- | --- |
| GOx-Gluteraldeyde/Pt-SWCNTs/PAA | 70 | 0.38 |
| GOx/PtNW-CNTs-chitosan/GCE | 30 | 3 |
| GOx/Pt-CNTs/TiO$_2$ | 0.24 | 6 |
| GOx-Gluteralderyde/Pt-MWCNTs/GCE | 52.7 | 30 |
| GOx-Pt-(sol-gel)/MWCNTs/CPE | 0.98 | — |
| Gox-Nafion-Pt-CNTs/GCE | — | 55 |

The first row of table 1 pertains to biosensor 120 described herein. Several aspects of utilizing carbon nanotubes and Pt nanoparticles over conventional materials in electrochemical glucose biosensing include increased effective surface area, enhanced mass transport of target analyte, and improved catalysis of redox agents. The high glucose sensitivity and low detection limit of the GOx-CNT/Pt nanosphere biosensor is related to the microenvironment created by the electrically connected network of CNTs and Pt nanospheres on the biosensor surface. The catalysis of enzymatic biosensors that utilize such nanostructures can be related to enhanced enzyme/biosensor charge transport including the ability to create a highly conductive electrical pathway to the redox center of immobilized enzymes. Such 'direct wiring' improves catalysis by obviating the need for diffusional electron mediators such as $H_2O_2$, thus allowing for electron exchange to occur directly between the redox center of the enzyme and the biosensor surface.

Figure 11A:
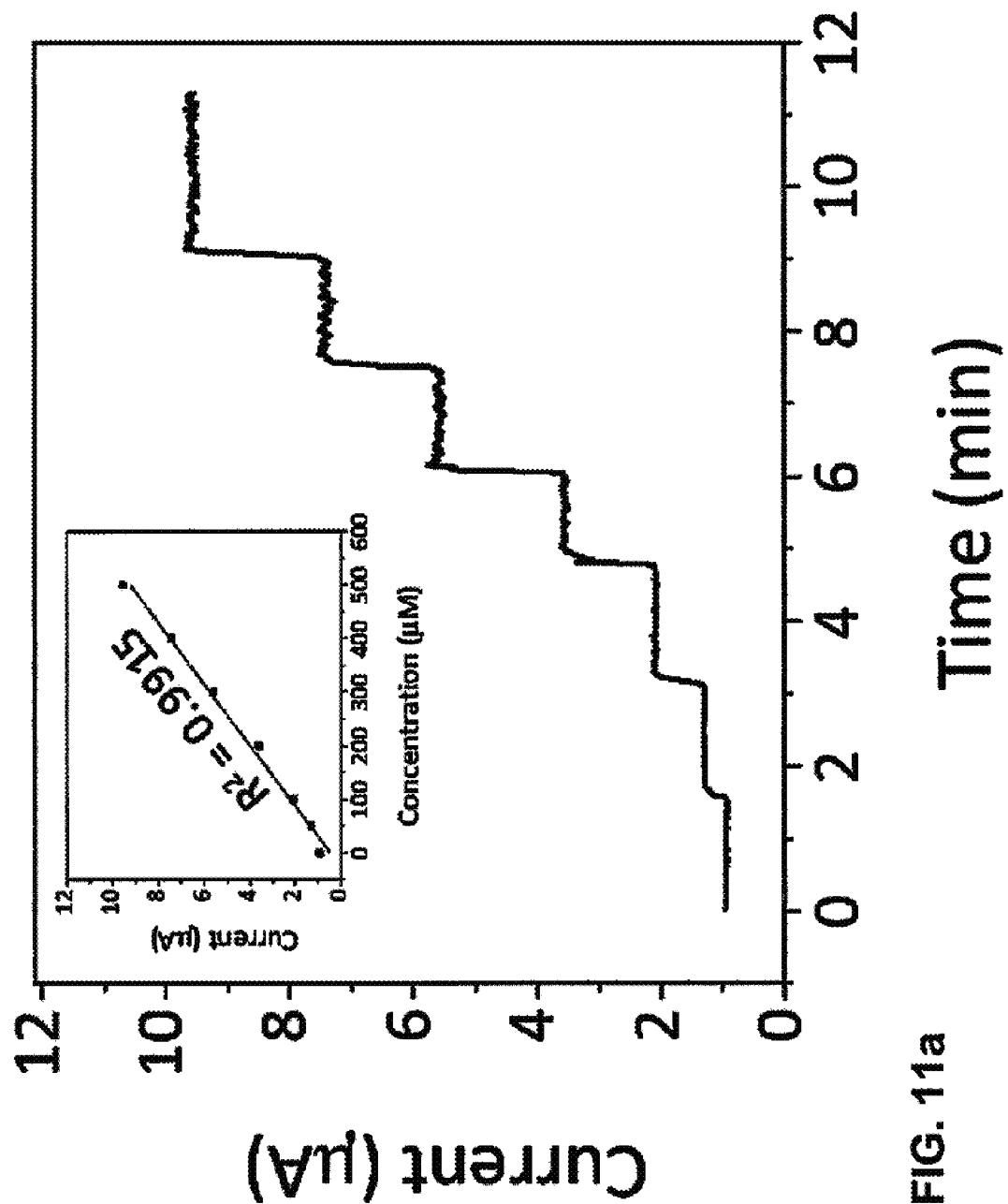
FIGS. 11a and 11b graphically represent electrical characteristics of a biosensor according to another embodiment of the present invention.
Figure 11B:
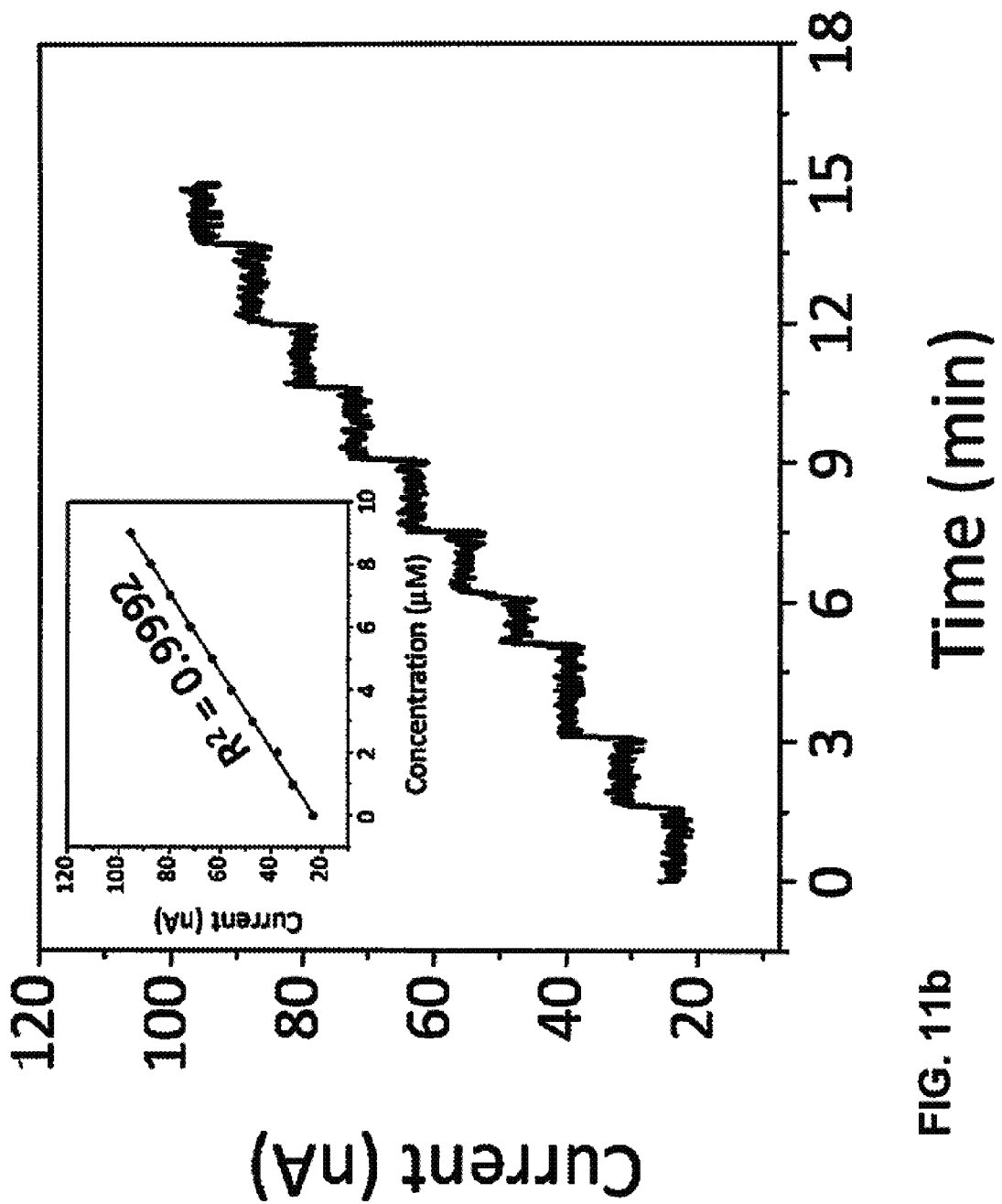

FIGS. 11a and 11b show amperometric glucose calibration experiments for the CNT/Pt nanosphere biosensor. The experimental detection limit graph (a) portrays the current response to eight successive concentration increases of 1 $\mu M$ while the micromolar calibration plot (b) portrays the current response to concentration increases of 50, 100, 200, 300, 400, and 500 $\mu M$ respectively. Insets display the linear regression analysis of the respective current versus concentration plots.

Figure 12:
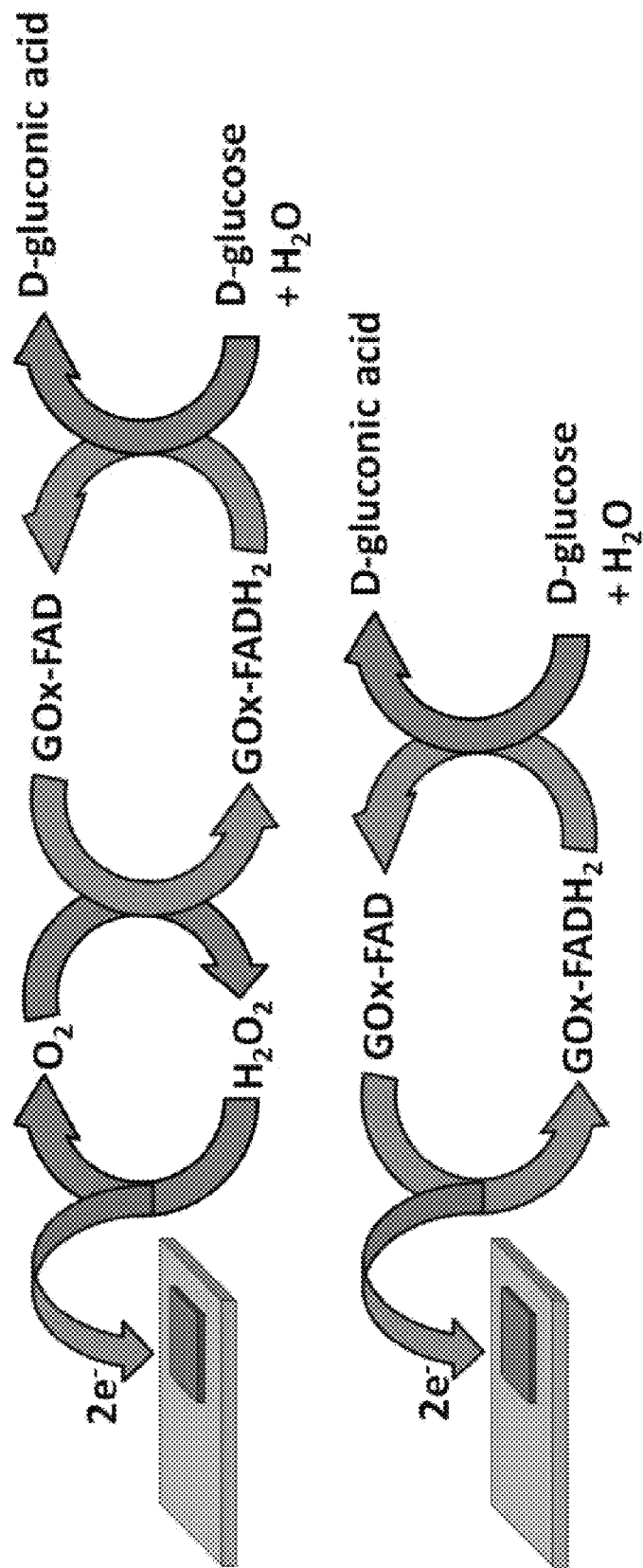
FIG. 12 shows electrochemical mechanisms of biosensor charge transport during the enzymatic breakdown of glucose via the enzyme GOx. The electron mediator $H_2O_2$ (top) shuttles electrons between the prosthetic group FAD of GOx to the biosensor surface while in direct electron environments (bottom) electron transfer occurs directly between the redox center ($FAD/FADH_2$) of GOx and the biosensor surface.
Figure 13:
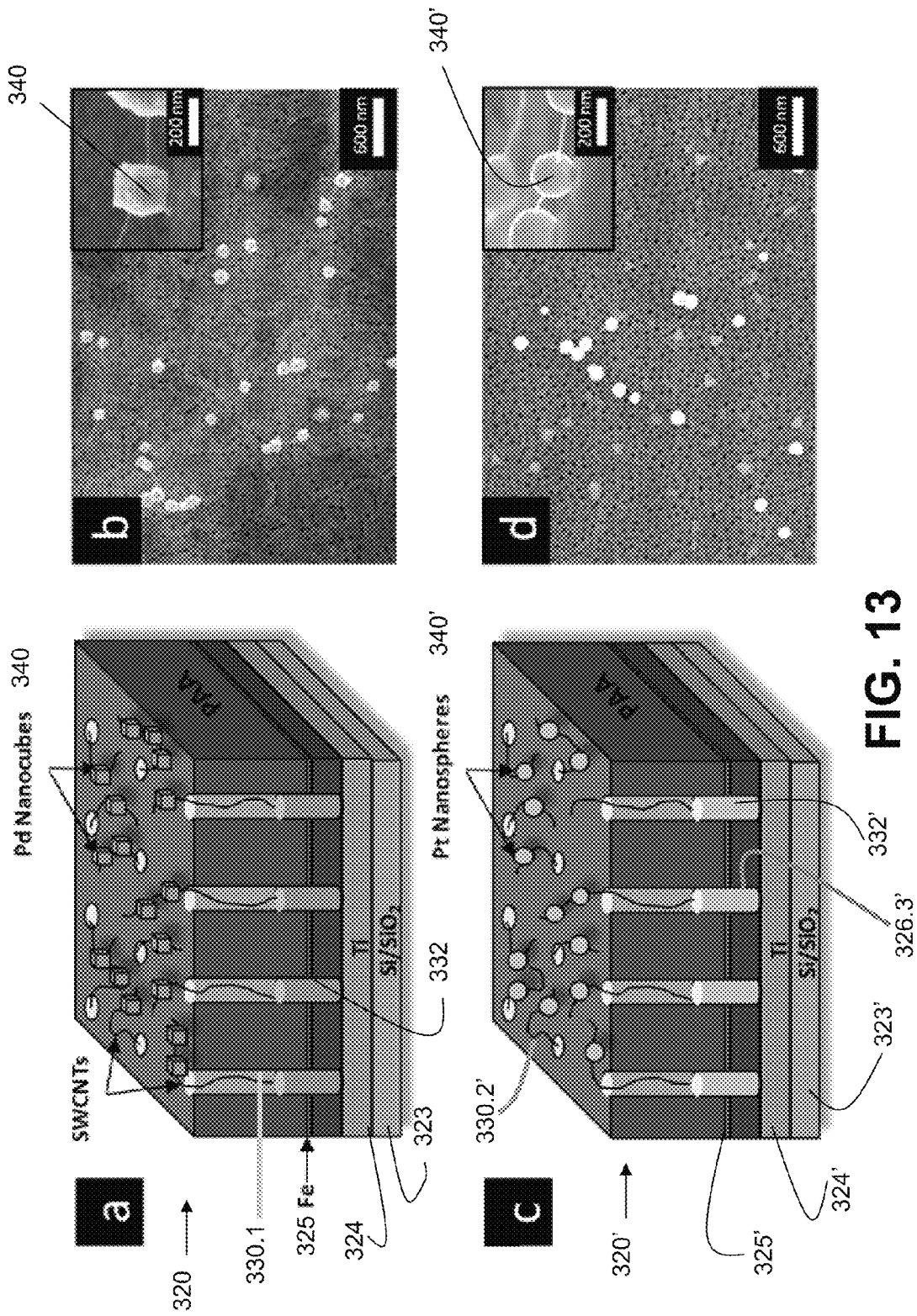
FIGS. 13a and 13b are schematic and photographic representations of a biosensor according to another embodiment of the present invention.
FIGS. 13c and 13d are schematic and photographic representations of a biosensor according to yet another embodiment of the present invention.

Furthermore, the direct electrical wiring of the redox center of GOx, the prosthetic group FAD, has been confirmed with GOx that has been cross-linked with gluteraldehyde (refer to FIG. 12). Thus it is possible that portions of the nanoscale network of CNTs and Pt nanospheres of the GOx-CNT/Pt biosensor are physically positioned within the electron tunneling distance of the GOx redox center. This close proximity would invoke direct electron exchange between the prosthetic group FAD of the enzyme, obviate the need for the $H_2O_2$ electron mediator, and heighten the amperometric sensitivity of the biosensor. In addition to charge transport via $H_2O_2$ oxidation (see Equations 1 and 2), direct charge transport via the enzyme redox center occurs for a portion of the immobilized GOx on the biosensor surface. These enhanced charge transport characteristics may explain the high sensitivity and low detection limit achieved during amperometric glucose experiments.

The CNT/Pt nanosphere biosensor demonstrates good glucose sensitivity (70 $\mu A\ mM^{-1}\ cm^{-2}$) and a relatively low detection limit 380 nM (S/N). The enhanced charge transport between the GOx enzyme and nanoscale biosensor and efficient charge conduction through Pt nanospheres electrically connected via CNTs are some reasons for the glucose sensing characteristics of the CNT/Pt nanosphere biosensor. Furthermore the in-situ fabrication protocol of the biosensor eliminates the need for extensive CNT and Pt nanoparticle processing steps.

FOURTH EXAMPLE

Single-walled carbon nanotubes (SWCNTs) have shown to facilitate direct electrochemistry of enzymes and demonstrate inherent electrocatalytic properties towards the oxidation of $H_2O_2$ and NADH, two enzymatic by-products measured during electrochemical glutamate sensing that are associated with the enzymes glutamate oxidase (GluOx) and glutamate dehydrogenase (GluDH) respectively. Furthermore CNTs immobilized on carbon nanotube-based electrodes show good biocompatibility and electrochemical properties towards on sensor neuronal growth and direct electrical neuronal stimulation, one indication that CNT-based biosensors have the potential to treat neurological disorders. Electrochemical glutamate biosensors based upon SWCNTs exhibit good sensing results in terms of sensitivity, detection limit, and response time. Furthermore, those based upon SWCNTs combined with metallic nanoparticles demonstrate good results.

Various embodiments of the present invention are represented by two SWCNT/metal nanoparticle glutamate biosensors 320 and 320' that are developed from the bottom-up with SWCNTs grown in-situ from a semi-ordered template fabricated on the sensing platform itself. The prime (') designation indicates that these inventive structures differ in terms of the material used for the nanowires and nanoparticles, as well as differences in the shape and size of the nanoparticles This templated growth of low-density SWCNTs are electrically connected in parallel via a Ti bottom back contact, thus creating a plurality of diffusional independent nanoelectrodes on the biosensor surface. The electrocatalytic noble metals, Pd and Pt, are electrodeposited on the SWCNTs to further enhance biosensor sensitivity. The Pd and Pt electrodeposition process forms distinctly shaped nanocubes and nanospheres at SWCNT defects. The size and spacing of the nanocube and nanosphere structures are tuned to provide electroactive surface area while still maintaining good inter-SWCNT distance for diffusional independence.

The two distinct Pd-SWCNT/PAA and Pt-SWCNT/PAA electrodes 320 and 320', respectively, are transformed into glutamate biosensors by immobilizing the enzyme glutamate oxidase (GluOx) within a matrix of gluteraldehyde and bovine serum albumin (BSA) through a facile drop coat method. This simple enzyme immobilization scheme not only reduces time and cost—it utilizes an oxidase enzyme, GluOx, that does not require enzyme cofactor replenishment during biosensor operation. Amperometric glutamate sensing results reveal that the GluOx/Pd-SWCNT/PAA biosensor 320 can out perform the GluOx/Pd-SWCNT/PAA biosensor 320' and similar CNT and CNT/nanoparticle-based electrochemical glutamate biosensors in terms of detection limit and overall linear sensing range. These results demonstrate a bottom-up approach towards SWCNT/metal nanoparticle-based biosensors that can be scaled for integration into implantable neuronal sensing devices.

The Pt nanosphere and Pd nanocube-SWCNT biosensors 320' and 320 are fabricated by following protocols similar to those previously discussed. The low-density SWCNT arrays are created from a porous template, porous anodic alumina (PAA), fabricated on an oxidized silicon wafer [P <100> Si (5 μm), $SiO_2$ (500 nm)]. In order to create the PAA template, a thin film metal stack 324 [Ti (100 nm), Al (100 nm), layer 325 of Fe (1 nm), and layers 326.1 and 326.2 of Al (the latter being 400 nm)] is e-beam evaporated onto the oxidized silicon wafer 323. The metalized substrate is subsequently anodized by immersion in 0.3M oxalic acid (5° C.) while being biased with 40V versus a Pt gauze auxiliary electrode. The anodization process creates semi-ordered pores 328 and 328' (20 nm dia.) that extend through the Al/Fe/Al layers to the Ti layer and converts the Al layers into the dielectric $Al_2O_3$.

An electrically conductive contact pad comprised of the evaporated metals is created for subsequent electrochemical processing and biosensing by leaving a portion of the sample un-anodized. SWCNTs are grown from the Fe catalyst layer 325 or 325' embedded within the pores of the PAA by a microwave plasma chemical vapor deposition (SEKI AX5200S MPCVD) technique that introduces methane ($CH_4$) gas to a hydrogen plasma environment at 900° C. The SWCNTs, 3-10 μm in length, extend vertically from the pores of the PAA and eventually come to rest horizontally on the PAA surface.

Pd nanocubes 340 (150 nm length) and Pt nanospheres 340' (150 nm dia.) are galvanostatically electrodeposited at SWCNT defect sites by a 3-electrode set-up (BASi Epsilon Cell Stand) in which pulsed currents (2-6 mA/cm$^2$ at 500 ms) are applied between the working electrode (SWCNTs/PAA) and auxiliary electrode (Pt gauze) within baths of 2 mM $PdCl_2$ and 15 mM $H_2PtCl_6$ respectively. The respective Pd and Pt electrodeposition also partially fills the pores of the PAA with nanowires 332 or 332', respectively—forming an electrical back contact to the SWCNTs by connecting the Ti bottom layer and Fe layer. The substrates are subsequently diced with a diamond-blade dicing saw (Disco DAD-2H/6) to create equally-sized (0.25 cm$^2$) Pd-SWCNT/PAA and Pt-SWCNT/PAA electrodes for electrochemical biosensing. FIGS. 13a, 13b, 13c, and 13d show tilted cross-sectional schematics with accompanying top-view field emission electron microscopy (FESEM) micrographs and side-view high magnification micrographs as insets portraying (a-b) the Pd-SWCNT/PAA 320 and (c-d) Pt-SWCNT/PAA electrodes 320'.

Nanomaterial enhanced electrochemical biosensors have several aspects that differ compared to more traditional macroelectrodes including: enhanced mass transport, high effective surface area, improved catalysis, decreased charging currents, and microenvironments more suitable for enzyme immobilization and enzyme/biosensor charge transport. Mass transport and effective surface area for both the Pd-SWCNT/PAA and Pt-SWCNT/PAA electrodes are influenced by the size and spacing of the respective Pd nanocubes 340 and Pt nanospheres 340' electrodeposited onto the SWCNT arrays.

In order to increase biosensor sensitivity through radial diffusion, nanoelectrodes contain numerous nanosized electrochemically active features that are separated by inert or dielectric material. Spacing parameters utilized to provide diffusionally independent nanoelectrodes span the range of six or ten times the radius of the nanoparticle to a guideline of 1 μM spacing between nanoelectrodes. In general, biosensors which adhere to these spacing parameters will experience enhanced mass transport by radial diffusion while those with smaller spacing intervals will experience linear planar diffusion where neighboring diffusion layers completely overlap. FIGS. 14a, 14b, and 14c are schematic diagram illustrating the relationship between the diffusion boundary layer and the spacing between electrochemically active nanoparticles on top of an inactive dielectric material. As spacing between adjacent nanoelectrodes decreases diffusion regions change from (a) radial, (b) transitional, and (c) linear. In the case of both the Pd-SWCNT/PAA and Pt-SWCNT/PAA electrodes, nanoelectrodes spacing is in part determined by spacing of the SWCNT defect sites.

Electron transfer across the generally inert SWCNT sidewalls occurs at carbon defect sites and accordingly low voltage/current electrodeposition of metallic nanoparticles onto SWCNTs preferentially nucleates at these defect sites. The average spacing of the Pt and Pd nanospheres on the Pd-SWCNT/PAA and Pt-SWCNT/PAA is 366 nm with a high standard deviation of 362 nm and overall spacing range between 50 nm and 1.2 μM, while on the other hand the average spacing between decorated SWCNTs is 8.0 μm (σ=6.1 μm) with the majority of SWCNT strand spacing falling within an overall range of 1 μm to 30 μm This metal nanoparticle spacing represents spacing preferred on the fabricated SWCNT arrays as lower voltage/current electrodepositions restrict metal to precipitate onto the SWCNT arrays and higher voltage/current electrodeposition may to deposit metal nanoparticles at higher densities including at non-defect sites. In an effort to maximize surface area and mass transport effects, the Pd and Pt nanocubes and nanospheres were designed to be 150 nm in width and diameter respectively. These dimensions provide diffusionally independent SWCNT strands that experience radial diffusion while maintaining a relatively high surface area for catalysis of redox species. Thus the Pd-SWCNT/PAA and Pt-SWCNT/PAA electrodes present a hybrid nanoelectrodes biosensor, where a balance is established between diffusional independence and surface area, in an overall effort to enhance electrochemical performance.

Figure 16A:
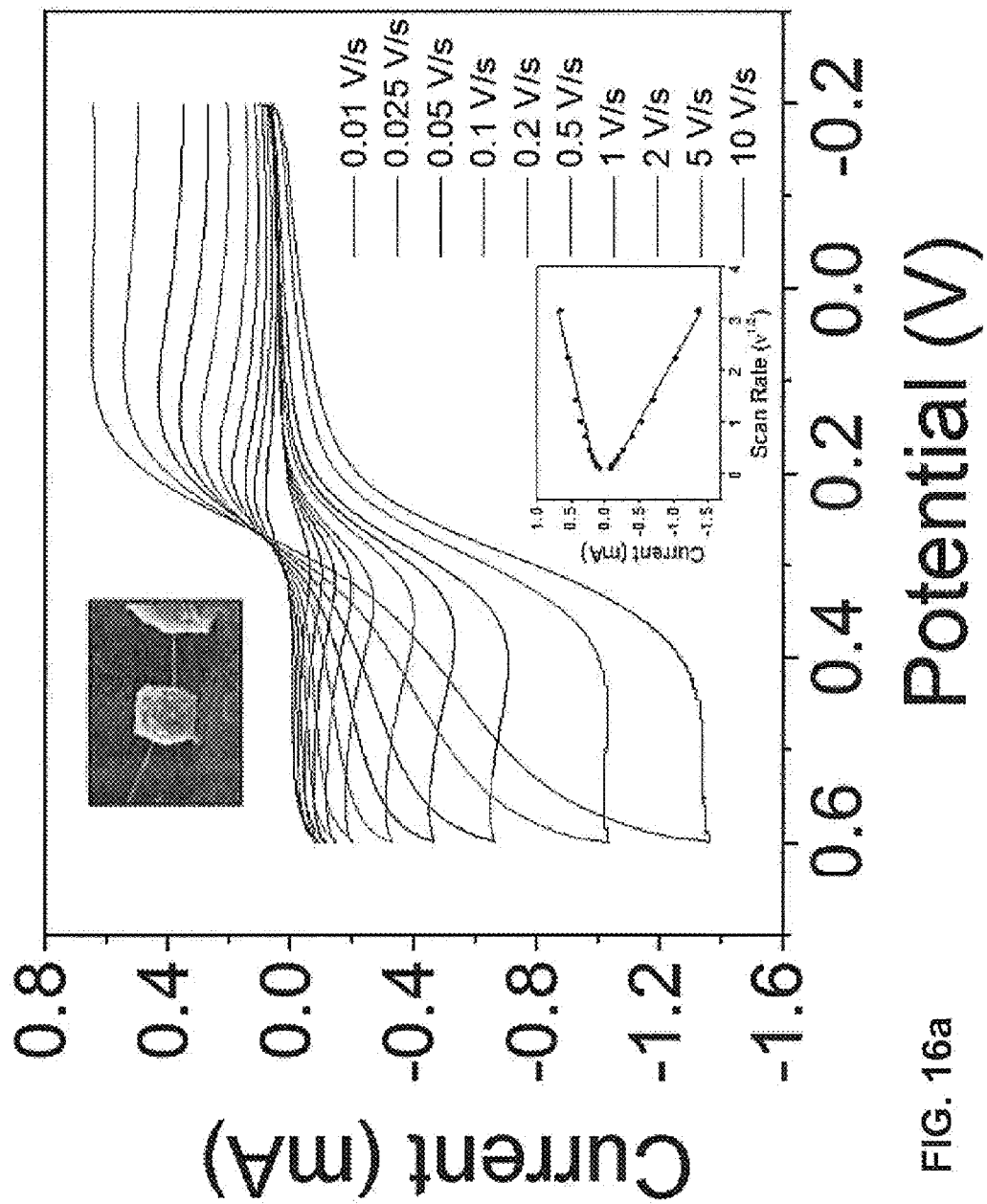
FIGS. 16a and 16b are graphical representations of the electrical characteristics of a biosensor according to one embodiment of the present invention.
Figure 16B:
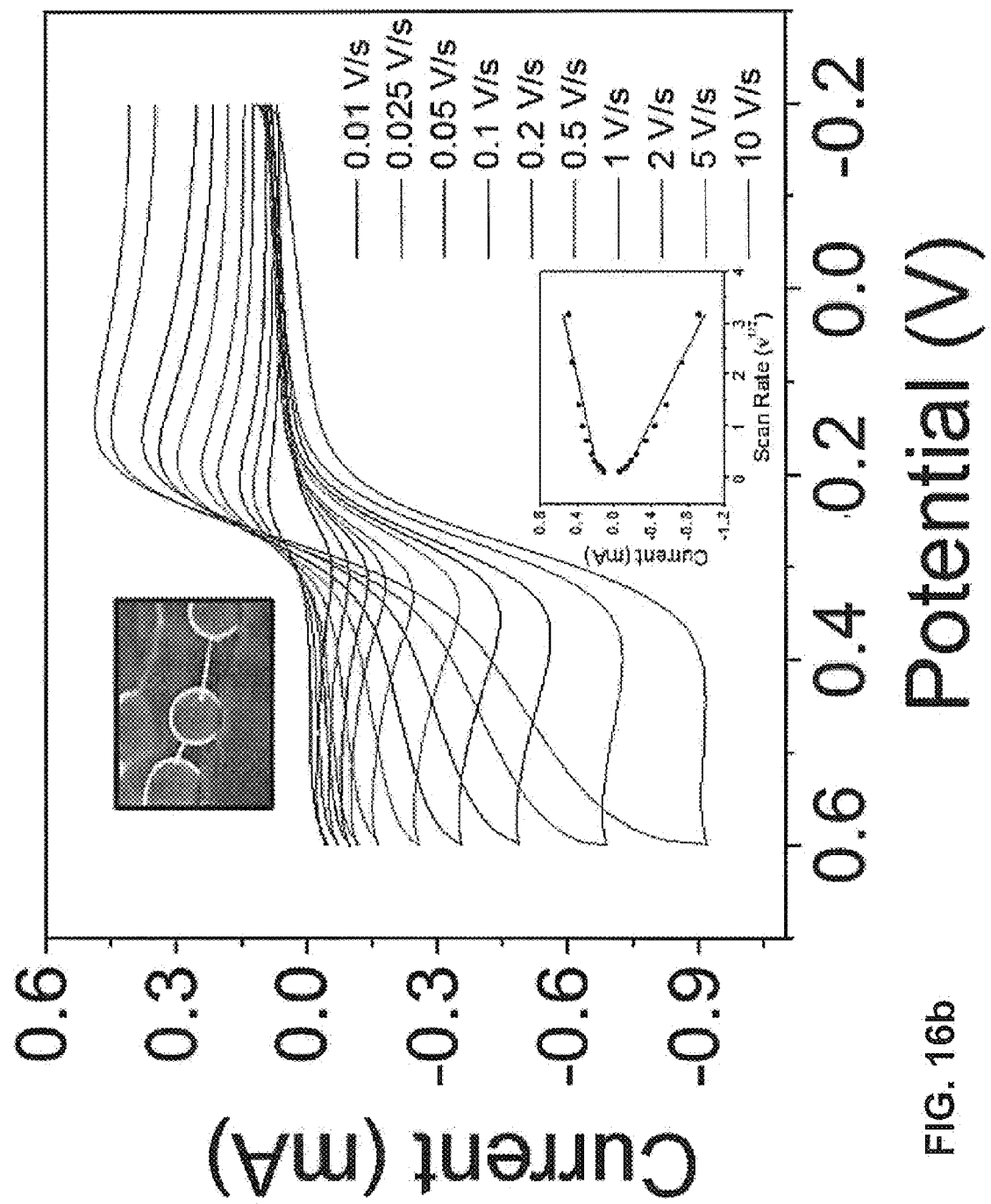

The electrochemical characterization of these hybrid structures is performed through ferricyanide cyclic voltammetry. The Pd-SWCNT/PAA and Pt-SWCNT/PAA electrodes are characterized via cyclic voltammetry in 4 mM Fe(CN)$_6^{3-}$ and 1 M KNO$_3$ at a potential scan that is cycled between −0.2V and 0.8V versus a Ag/AgCl reference electrode at varying scan rates. FIGS. 16a and 16b are cyclic Voltammograms of the (a) Pd-SWCNT/PAA and (b) Pt-SWCNT/PAA electrodes in 4 mM Fe(CN)$_6^{3-}$ and 1 M KNO$_3$ at a potential scan that is cycled between −0.2V and 0.8V versus a Ag/AgCl reference electrode at varying scan rates. Insets portray the linear relationship between peak reduction and oxidation peaks to the square root of the scan rate.

The cyclic voltammograms of the Pt-SWCNT/PAA electrode shows well-defined oxidation and reduction peaks due to the Fe$^{II}$(CN)$_6^{4-}$/Fe$^{III}$(CN)$_6^{3-}$ redox couple starting at +0.30V and +0.23V at a scan rate of 10 mV/s and gradually shifting to +0.37V and +0.16V at 2 V/s respectively. Likewise the Pd-SWCNT/PAA electrode demonstrates similar well-defined oxidation and reduction peaks at +0.30V and +0.23V at 10 mV/s and +0.36V and +0.17V at 2 V/s. As the scan rate increases the potential gap between the peak reduction and oxidation currents increases, denoting a shift from a reversible reaction in which the forward and backward scans superimpose to one that is quasireversible in which the scans appear more sigmoidal in shape with a developing diffusion-limited current plateau typical of nanoelectrodes arrays. This shift in cyclic voltammogram morphology and its subsequent increase in current density is a direct response to the mass transport kinetics of the hybrid SWCNT/nanoparticle design.

Figure 14:
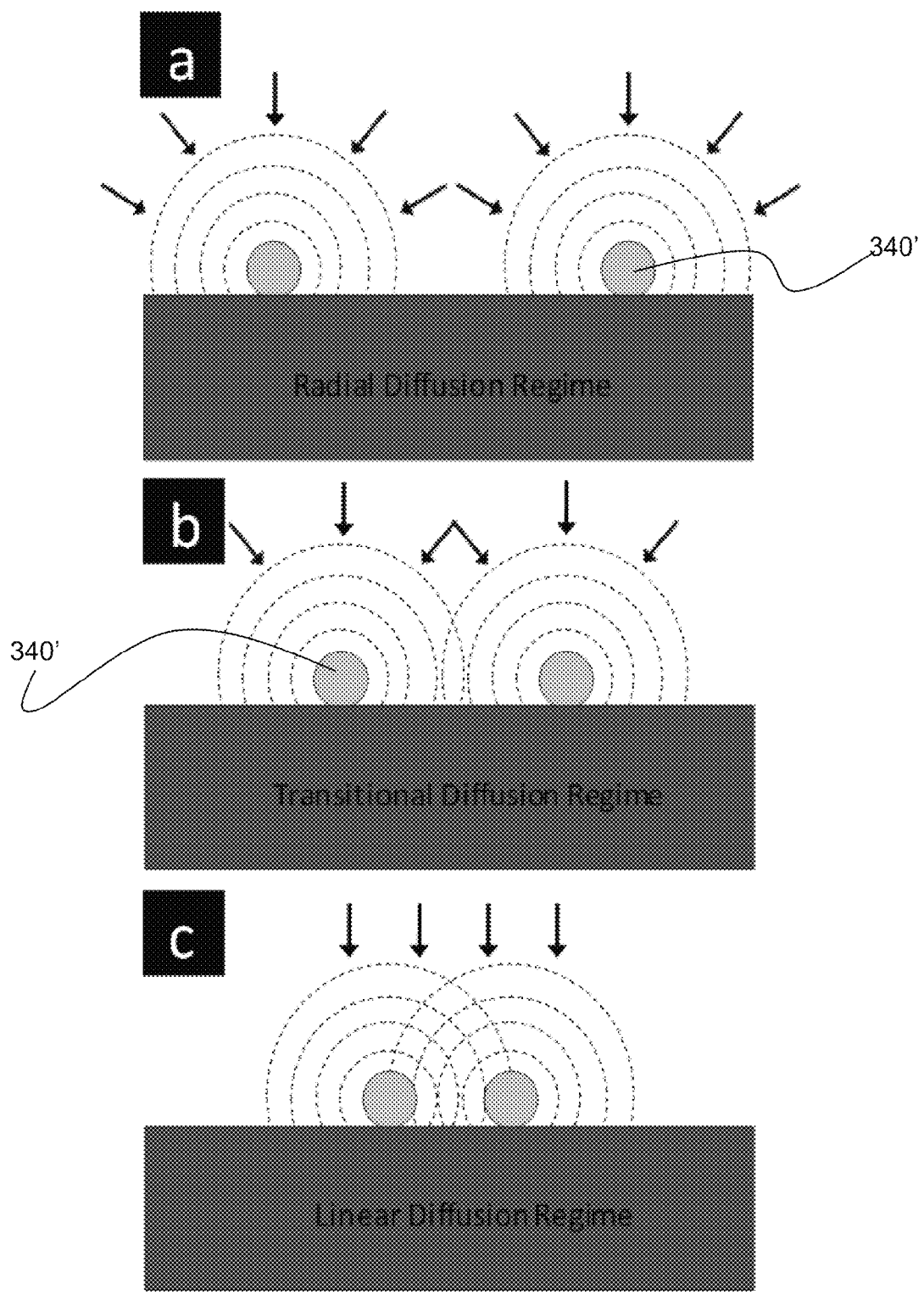
FIGS. 14a, 14b, and 14c are schematic representations of different types of diffusion.

At slower scan rates the mass depletion region around each conducting metallic nanoparticle grows until adjacent depletion regions from neighboring nanoparticles overlap leading to mass transport within the linear region (See FIG. 14).

Figure 15:
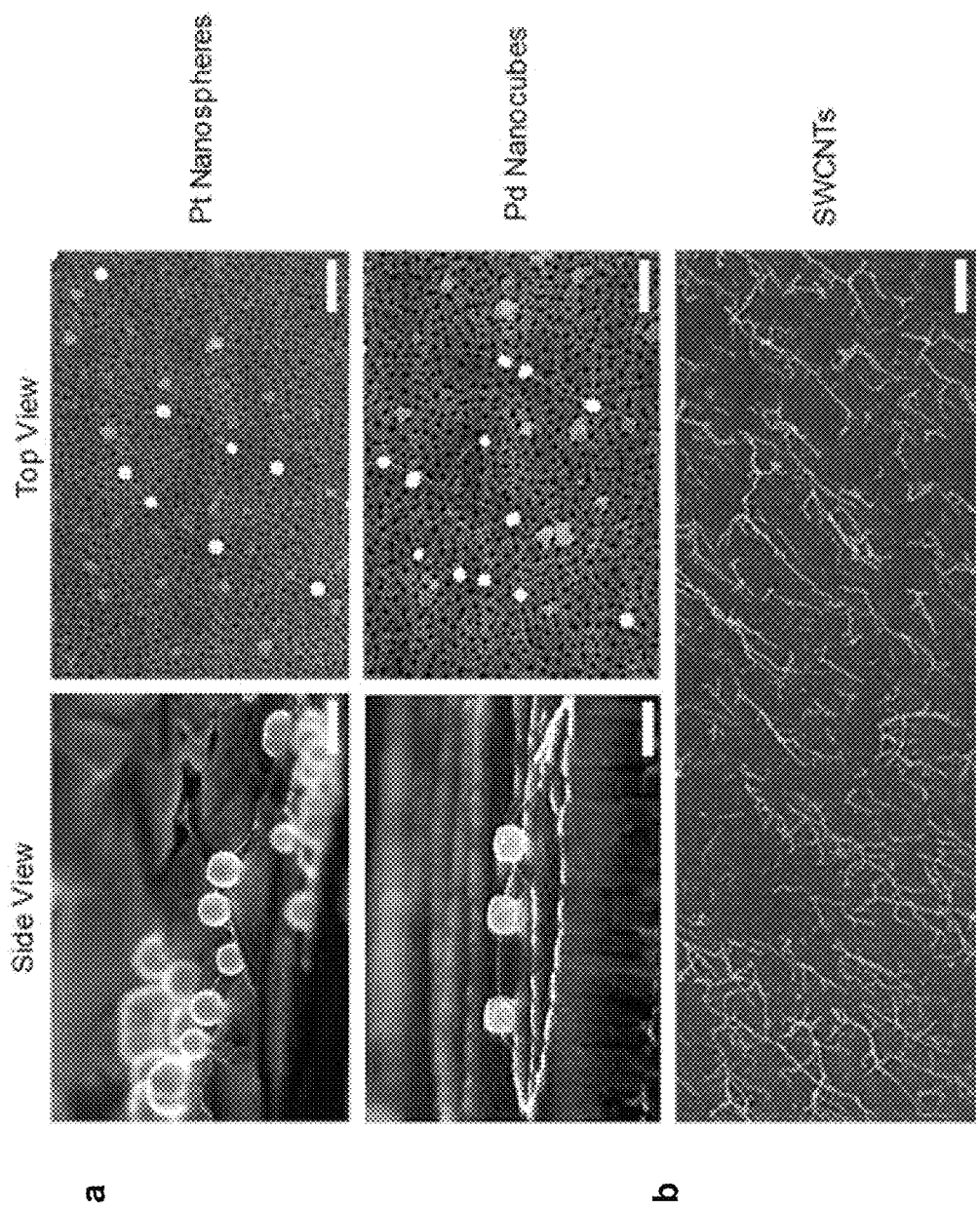
FIGS. 15a and 15b are photographic representations of portions of the apparatus of FIG. 13c.

FIGS. 15a and 15b show top view and side-view FESEM micrographs of Pt nanospheres and Pd nanocubes electrodeposited on SWCNT arrays on PAA illustrates the typical distance between metallic nanoparticles on individual SWCNT strands. (b) The distance between SWCNTs strands is portrayed in the top-view FESEM micrograph of SWCNTs resting on PAA. SWCNTs were coated with electrodeposited Pd in order to visually observe the SWCNTs with FESEM. Top-view and side-view Pt nanosphere and Pd nanocube FESEM micrograph scale bars (a) correspond to 500 nm and 300 nm respectively while the top-view SWCNTs FESEM micrograph scale bar (b) corresponds to 20 μm.

The increased current densities associated with higher scan rates are indicative of radial diffusion as diffusion boundary layers have had less time to expand and reach the boundary layers of neighboring particles. Furthermore, the reduction and oxidation current peaks vary linearly to the square root of the scan rate (See insets of FIG. 16), typical of fast heterogeneous charge transfer occurring between the redox solution and the biosensor surface.

Thus the electroactive surface area of the SWCNT/Pd and SWCNT/Pt biosensors can be calculated by using the Randles-Sevcik equation (6):

$$i_p = 2.69 \times 10^5 A D^{\frac{1}{2}} n^{\frac{3}{2}} v^{\frac{1}{2}} C \tag{6}$$

where n is the number of participating electrons in the redox reaction (n=1), A is the electrode area (cm$^2$), D is the diffusion coefficient of the molecule in solution (6.70×10$^{-6}$ cm$^2$ s$^{-1}$), C is the concentration of the target molecule in the bulk solution (4 mM), v is the scan rate (V s$^{-1}$), and i$_p$ is the current (A) at the reduction peak. The calculated effective electrocatalytic surface area for the Pt-SWCNT/PAA and Pd-SWCNT/PAA electrodes is nearly identical, (2.27±0.2)×10$^{-4}$ cm$^2$ and (3.13±0.2)×10$^{-4}$ cm$^2$ respectively. This similar effective surface area of both the Pd nanocube and Pt nanosphere augmented electrodes presents a more precise electrochemical performance comparison in subsequent glutamate sensing.

The SWCNT/Pd and SWCNT/Pt biosensors 320 and 320', respectively, were both employed as electrochemical glutamate biosensors by immobilizing the enzyme glutamate oxidase (GluOx) on the electroactive surface of the biosensors. The GluOx enzyme is immobilized on the sensor surface by first mixing it with a 1% (w/v) bovine serum albumin (BSA) solution. The GluOx/BSA mixture is subsequently cross-linked with gluteraldehyde by adding 0.125% (w/v) gluteraldehyde. The gluteraldehyde forms covalent bonds with the BSA and GluOx mixture, preventing enzyme leakage. Furthermore gluteraldehyde aids in adhesion, allowing the immobilized GluOx/BSA solution to adhere to the electroactive SWCNT/metal nanoparticle surface. The BSA binds to excess gluteraldehyde within the mixture, preventing the excess gluteraldehyde from denaturing the GluOx enzyme.

The GluOx/BSA/gluteraldehyde solution is drop coated onto the surface of the electrode and allowed to dry several hours at room temperature before electrochemical sensing. Biofunctionalized electrodes are stored at 4° C. when electrochemical experimentation is not being performed.

Electrochemical glutamate biosensors biofunctionalized with the enzyme GluOx typically measure glutamate concentrations via the electrocatalytic detection of hydrogen peroxide produced during the GluOx/glutamate reaction. The chemical reactions associated with the enzymatic breakdown of L-glutamate and the subsequent oxidation of the hydrogen peroxide (H$_2$O$_2$) produced from this reaction are as follows:

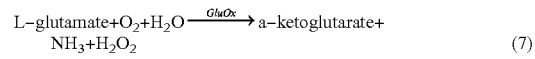

$$\text{L-glutamate} + O_2 + H_2O \xrightarrow{GluOx} \alpha\text{-ketoglutarate} + NH_3 + H_2O_2 \tag{7}$$

$$H_2O_2 \rightarrow 2H^+ + O_2 + 2e^- \tag{8}$$

In order to demonstrate the effectiveness of the biofunctionalized GluOx/Pd-SWCNT/PAA and GluOx/Pt-SWCNT/PAA towards electrochemical glutamate biosensing, both sensors are first utilized in amperometric H$_2$O$_2$ sensing. All electrochemical measurements are performed in 20 mL of phosphate buffer solution (PBS) with a pH of 7.4 via a 3 electrode set-up (BASi Epsilon Cell Stand) where a biofunctionalized electrode acts as the working electrode (320" or 320'"), Pt wire as the auxiliary electrode 361, and Ag/AgCl as the reference electrode 362. Successive 20 μL aliquots of H$_2$O$_2$ are added to the PBS buffer solution to increase the peroxide concentration by 10 μM increments while the redox current associated with the oxidation of H$_2$O$_2$ at a working potential of 350 mV is measured.

Figure 17:
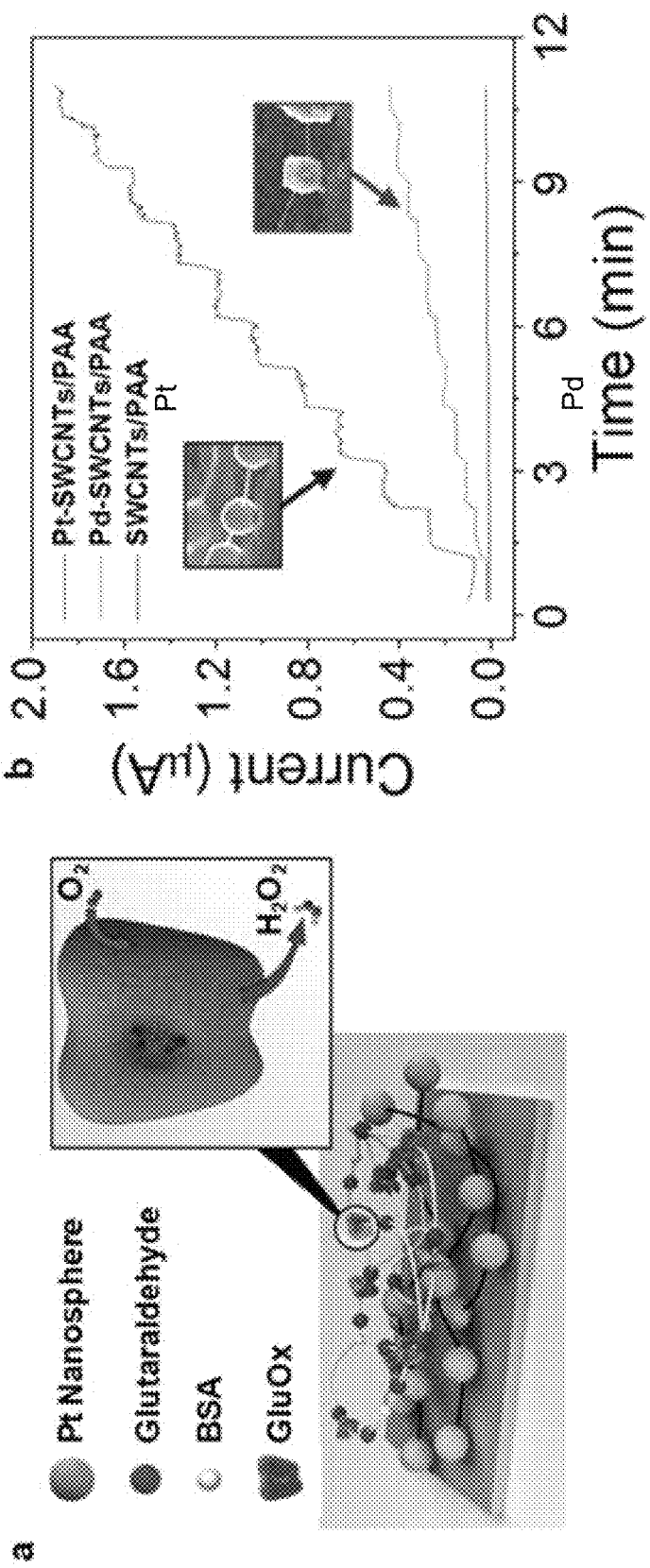
FIG. 17 is a graphical representation of the electrical characteristics of a biosensor according to another embodiment of the present invention.

Referring to FIG. 17, there can be seen a side-view schematic diagram illustrating GluOx cross-linked with gluteraldehyde and BSA immobilized on networks of Pt nanospheres connected by SWCNTs (black lines). The insert shows a magnified view of a single GluOx. Glutamate binds within the enzymatic pocket of GluOx while O2 is consumed and the electrochemical transducer H2O2. FIG. 17b graphically shows results from amperometric sensing of H2O2 oxidation in 20 mL of PBS (pH 7.4) using a three electrode potentiostat with an applied working potential of 350 mV. The current response for incremental H2O2 concentration increases of 10

µM are recorded for the GluOx/Pt-SWCNT/PA (blue), GluOx/Pd-SWCNT/PAA (red), and GluOx/SWCNTs/PAA (black) biosensors.

The GluOx/Pt-SWCNT/PAA biosensor 320' exhibited a sensitivity of 72.4 µA mM$^{-1}$ cm$^{-2}$ towards the oxidation of H$_2$O$_2$, which is over four times the sensitivity of the GluOx/Pd-SWCNT/PAA biosensor 320 (16.8 µA mM$^{-1}$ cm$^{-2}$). The GluOx/SWCNTs/PAA displays a negligible response towards H$_2$O$_2$ because the SWCNTs are not electrically contacted to the Ti bottom layer 324 because Pd or Pt electrodeposition has not been performed.

Figure 18C:
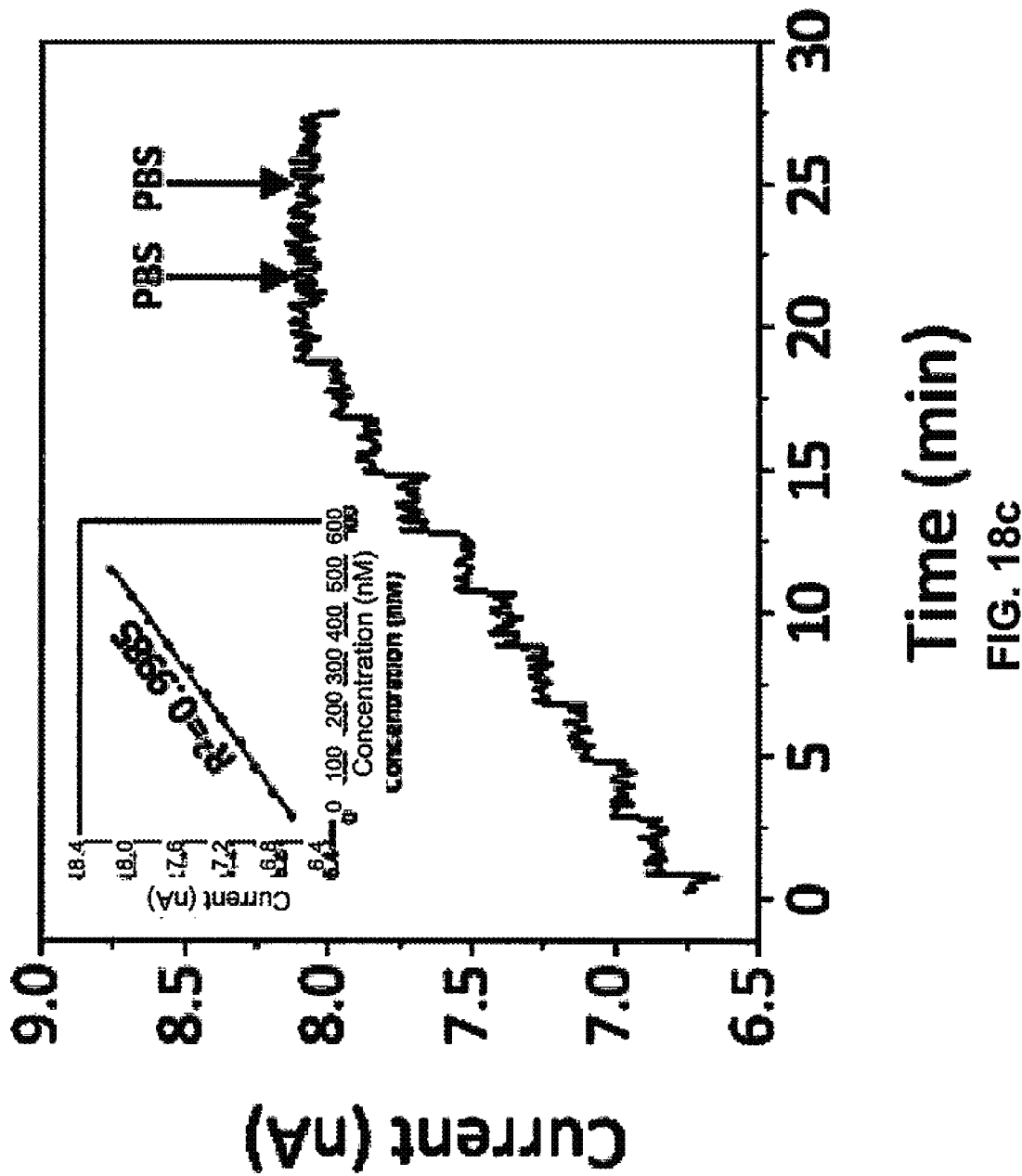
FIGS. 18c and 18f are enlargements of portions of the graphical representations of FIGS. 18b and 18e, respectively.
Figure 18F:
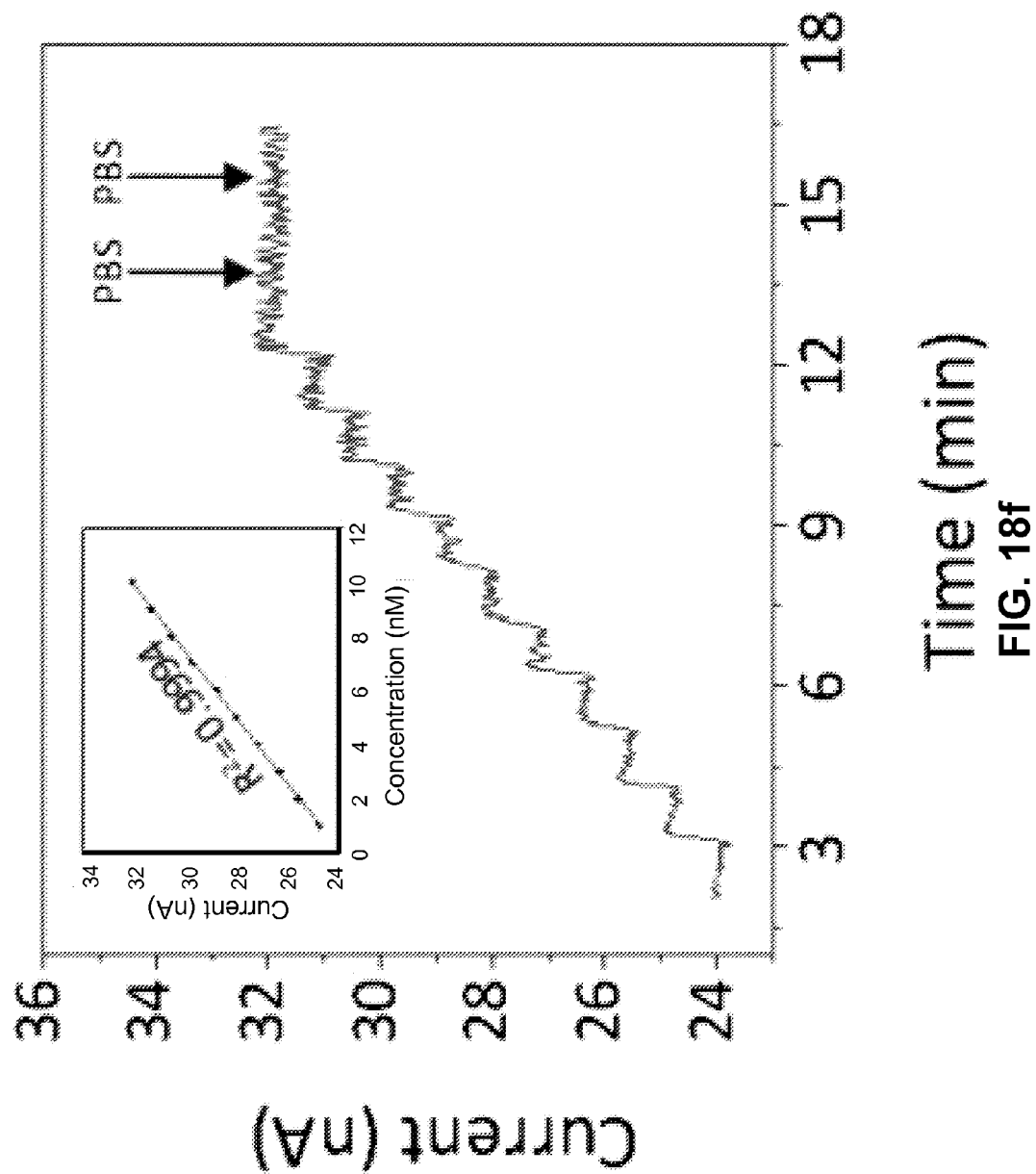

Amperometric glutamate sensing for both the GluOx/Pd-SWCNT/PAA and GluOx/Pt-SWCNT/PAA biosensors is conducted under the same 3-electrode set-up and working potential established for the amperometric H$_2$O$_2$ testing. Amperometric glutamate calibration plots for both sensors are created by adding successive aliquots of increasing glutamate concentrations while measuring the corresponding current response of the biosensor (See FIG. 18.). The amperometric glutamate calibration plots (FIGS. 18a and 18d) and experimental detection limit plots (FIGS. 18c and 18f) are illustrated. As a control experiment, the buffer media PBS is injected during amperometric testing at equivalent volumes as the glutamate injections to demonstrate the selectivity of the biosensors towards L-glutamate even at the lowest detectable glutamate concentration steps (See FIGS. 18c and 18d).

FIGS. 18a, 18b, 18c, 18d, 18e, and 18f show the results of amperometric glutamate calibration experiments for the (a-c) GluOx/Pt-SWCNT/PAA and (d-e) GluOx/Pd-SWCNT/PAA are performed with a three electrode potentiostat at a working potential of 350 mV. Current response (a) for the GluOx/Pt-SWCNT/PAA for successive L-glutamate concentration increases of 100-500 nM by 100 nM increments, 1-5 µM by 1 µM increments, 10-50 µM by 10 µM increments, 100-500 µM by 100 µM, and finally 1-5 mM by 1 mM increments while inset portrays linear sensing region. Current response (b) for the GluOx/Pd-SWCNT/PAA for successive L-glutamate concentration increases of 2-5 µM by 1 µM increments, 10-50 µM by 10 µM increments and 100-500 µM by 100 µM while inset portrays linear sensing region. Corresponding magnified views, (b) and (e), of the lower end of the respective calibration plots portraying a portion of the linear sensing region with insets showing linear regression analysis of the current vs. concentration profiles. Current response for 10 successive 20 µL glutamate injections resulting in incremental concentration increases of 50 nM (c) and 1 µM (f) followed by two 20 µL injections of PBS for the respective biosensors, while insets show linear regression analysis of the current vs. concentration profiles.

The GluOx/Pt-SWCNT/PAA biosensor exhibited a wide linear sensing region extending from 50 nM to 500 µM with a theoretical detection limit of 7.6 nm (3σ) while the GluOx/Pd-SWCNT/PAA biosensor portrayed a linear sensing region from 1 to 90 µM with a theoretical detection limit of 180 nM (3σ). Furthermore the GluOx/Pt-SWCNT/PAA biosensor experiences a L-glutamate sensitivity (27.4 µA mM$^{-1}$ cm$^{-2}$) that is five times the sensitivity of the GluOx/Pd-SWCNT/PAA biosensor (5.5 µA mM$^{-1}$ cm$^{-2}$). The response time (t$_{90\%}$) was 8 seconds for both biosensors. These experimental results demonstrate the effectiveness of the low density SWCNT/metal nanoparticles biosensors in amperometric glutamate biosensing and their sensing capabilities proved good when compared to other electrochemical glutamate biosensors (See Table 2.). Furthermore these results demonstrate the capability of both the GluOx/Pt-SWCNT/PAA and GluOx/Pd-SWCNT/PAA biosensors to effectively measure glutamate concentrations within the 1-2 µM extracelluar concentration range found within brain tissue via microdialysis, and the potential to detect at considerably lower concentration limits which is of importance because recent reports suggest glutamate concentrations may be considerably lower in brain tissue than those estimated by microdialysis.

TABLE 2

Electrochemical performance comparison of CNT/metallic nanoparticle, CNT, and non-nanomaterial based glutamate biosensors.

| Biosensor Description | Detection Limit [nM] | Linear Range [µM] | Response Time [s] |
|---|---|---|---|
| GLOx/Pt-SWCNTs/PAA | 7.6 | 0.05-500 | 8 |
| GLOx/Pd-SWCNTs/PAA | 180 | 1-90 | 8 |
| Ferrocene/SWCNTs/Pt Wire | — | 1-7 | 3 |
| GIDH-Th-SWCNTs/GC | 100 | 0.5-400 | 5 |
| (GLDH/Pt-PAMAM)$_N$/CNTs | 10 | 0.2-250 | 3 |
| (GLDH/Pt-DENs)$_N$/CNTs | 10 | 0.1-60 | 3 |
| GLOx-PVA-SbQ-Glut/Pd | 50 | 0.5 to 100 | 20 |
| GmOX-CHIT/Pt | 100 | 0.5-200 | 2 |
| GLOx-HRP-PEGDGE/Au | 500 | up to 60 | 35 |
| GLOD/Nafion ®/MV GC | $2 \times 10^4$ | up to 75 | — |

The top two rows of Table 2 refer to biosensors 340' and 340, respectively, described in this document. One embodiment of the present invention, the GluOx/Pt-SWCNT/PAA biosensor, outperformed a biosensor according to another embodiment of the present invention, the GluOx/Pd-SWCNT/PAA biosensor, and further showed good performance relative to all other nanomaterial enhanced amperometric glutamate biosensors in terms of detection limit and linear sensing range. Biosensor according to various embodiments of the present invention can be attributed to several parameters including: the electrocatalytic nature of Pt towards the oxidation of H$_2$O$_2$, the high surface-to-volume ratio of the SWCNTs and metallic nanoparticles that promotes high charge transfer, and the radial diffusion to the metal nanoparticle decorated arrays of SWCNTs. Additionally, the glutamate sensitivity of the GluOx/Pt-SWCNT/PAA biosensor is nearly 5 times greater than that exhibited by the GluOx/Pd-SWCNT/PAA, while the amperometric H$_2$O$_2$ sensing results illustrate an approximate sensitivity disparity factor of four between the respective biosensors.

Figure 23:
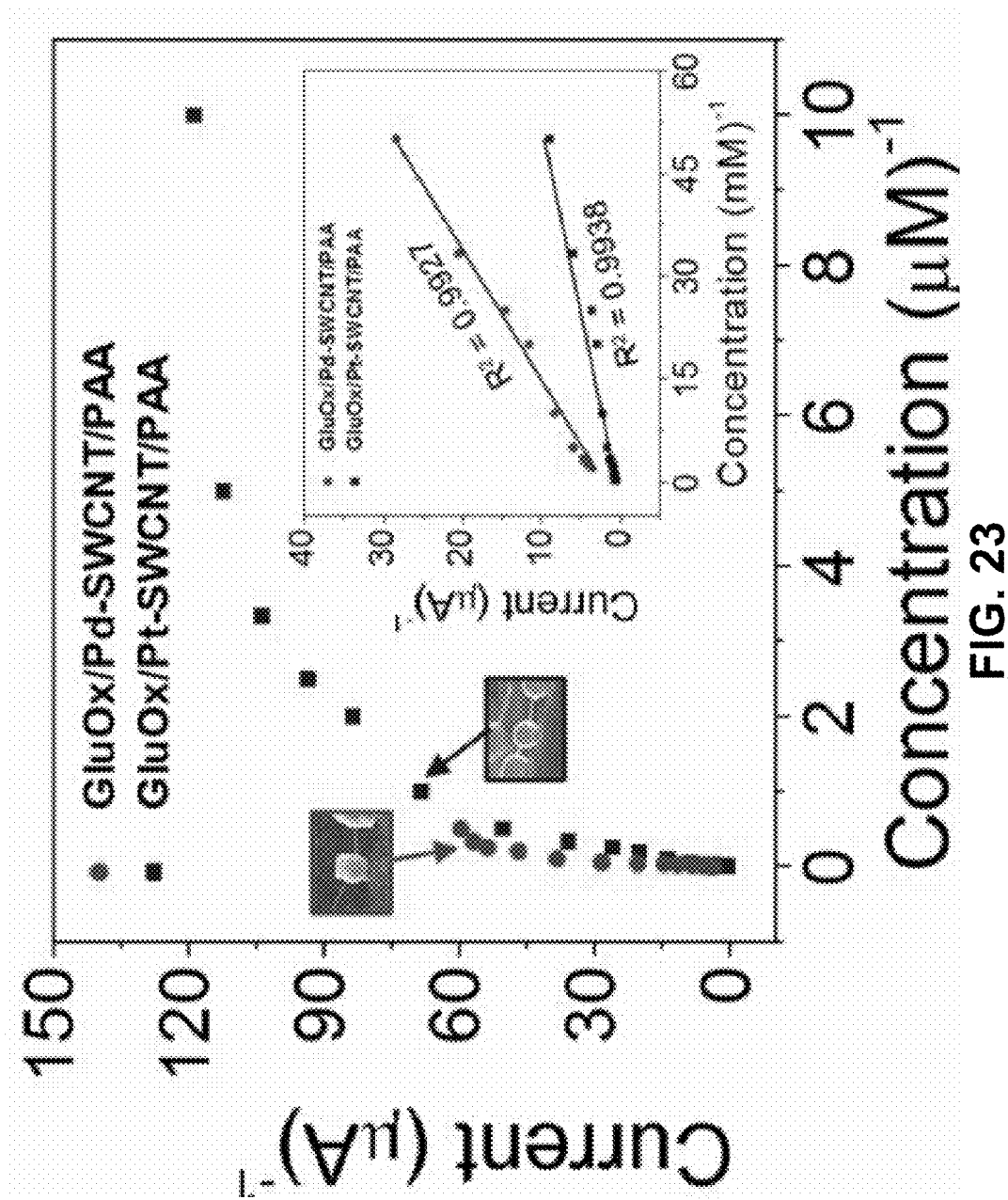
FIG. 23 is a graphical representation of the electrical characteristics of a sensor according to one embodiment of the present invention.

The Michealis-Menten hyperbolic relationship between enzymatic rate and substrate concentration is often analyzed in order to monitor the kinetics of free or captured enzymes. In order to evaluate the enzyme-substrate kinetics involved during immobilized enzyme on the biosensor surface interface, the effective or apparent Michealis-Menten constant (K'M) can be calculated amperometrically from the Lineweaver-Burk type equation $$\frac{1}{i_{ss}} = \left(\frac{K'_m}{i_{max}}\right)\left(\frac{1}{C}\right) + \left(\frac{1}{i_{max}}\right) \tag{9}$$

where imax is the current measured during analyte saturation and iss is the measured steady-state current associated with a given concentration (C). The double reciprocal Lineweaver-Burk plot (FIG. 23) offers a phenomenological description of the enzyme kinetics of the immobilized GluOx enzyme on both the GluOx/Pt-SWCNT/PAA and GluOx/Pd-SWCNT/PAA biosensors as imax and K'M is evaluated by analyzing the plot slope and y-intercept in conjunction with Equation (9).

According to the linear fit of the linear portion of the Lineweaver-Burk plot (FIG. 23) the apparent imax and K'M were evaluated to be 780 nA and 78.2 μM for the GluOx/Pt-SWCNT/PAA biosensor and 364 nA and 184 μM for the GluOx/Pd-SWCNT/PAA biosensor. The K'M of both biosensors is substantially lower than the 700 μM reported by a poly(ophenylenediamine) modfied Pt wire microelectrode, the 776 μM reported by a sol-gel modified Pt microelectrode, the 2.84 mM reported by a glassy carbon electrode modified with Nafion® and methyl viologen, and the 3.0 mM reported by graphite rods modified with a redox hydrogel, suggesting that the networks of SWCNTs modified with Pt nanospheres and Pd nanocubes of the GluOx/Pt-SWCNT/PAA and GluOx/Pd-SWCNT/PAA biosensors respectively creates an unique nanoenvironment well-suited for enzymatic biosensing.

These sensitivity results corroborate the hypothesis that the low-density SWCNT/Pt nanosphere arrays create a microenvironment that is amenable to the tertiary structure of the enzyme allowing for enzyme activity. Such a microenvironment creates a low resistance pathway for glutamate diffusion and subsequent oxidation of $H_2O_2$ close to the conducting nanoparticle/SWCNT surface for possible direct electron transfer between the GluOx cofactor, flavin adenine dinucleotide (FAD), and the biosensor surface.

While the inventions have been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. An apparatus comprising:
   a substrate including an electrically conductive layer and an electrically insulating layer, the insulating layer including a plurality of pores each having a first end and second open end and a passage therebetween, the first end of each pore being open to the conductive layer;
   a plurality of carbon nanotubes each having first and second ends, each said nanotube being grown within a different one of said pores, the first end of each said nanotube being in electrical contact with said conductive layer, the second end of each said nanotube extending out of the second open end of the respective pore; and
   a plurality of nanoparticles, each said nanoparticle being electrodeposited to the extension of a different one of said nanotubes, each said nanoparticle having bonded to it an enzyme for converting a substance into products
   which further comprises a plurality of electrically conductive nanowires, each said nanowire being located within a different one of said pores and providing electrical continuity from the respective nanotube of the pore to said conductive layer.

2. The apparatus of claim 1 wherein said nanoparticle is one of a nanosphere or nanocube.

3. The apparatus of claim 1 wherein said nanoparticle comprises platinum or palladium.

4. The apparatus of claim 1 which further comprises a layer of gold electrodeposited on each said nanoparticle.

5. The apparatus of claim 1 wherein said enzyme is covalently bonded to said nanoparticle.

6. The apparatus of claim 1 wherein said enzyme is bonded to said nanoparticle by a thiol linker.

7. The apparatus of claim 1 wherein the substance is glucose and the enzyme is glucose oxidase.

8. The apparatus of claim 1 wherein the substance is glutamate and the enzyme is glutamate oxidase.

9. The apparatus of claim 1 wherein the substance is glutamate and the enzyme is glutamate dehydrogenase.

10. The apparatus of claim 1 wherein at least one of the products is hydrogen peroxide.

11. The apparatus of claim 1 wherein said insulating layer comprises porous anodic alumina.

12. The apparatus of claim 1 wherein a characteristic overall average length of said nanoparticles is more than about 100 nanometers and less than about 300 nanometers.

13. The apparatus of claim 1 wherein said conductive layer comprises titanium.

14. The apparatus of claim 1 wherein the carbon nanotube is a single walled carbon nanotube.

15. The apparatus of claim 1 wherein the carbon nanotube is a multiwalled walled carbon nanotube.

16. An apparatus comprising:
    a substrate including an electrically conductive layer and an electrically insulating layer, the insulating layer including a plurality of pores each having a first end and second open end and a passage therebetween, the first end of each pore being open to the conductive layer;
    a plurality of carbon nanotubes each having first and second ends, each said nanotube being grown within a different one of said pores, the first end of each said nanotube being in electrical contact with said conductive layer, the second end of each said nanotube extending out of the second open end of the respective pore; and
    a plurality of nanoparticles, each said nanoparticle being electrodeposited to the extension of a different one of said nanotubes, each said nanoparticle having bonded to it an enzyme for converting a substance into products
    wherein said substrate includes a catalytic layer placed in between said conductive layer and said insulating layer, and said nanotubes are grown from said catalytic layer.

17. The apparatus of claim 16 wherein said nanoparticle is one of a nanosphere or nanocube.

18. The apparatus of claim 16 wherein said nanoparticle comprises platinum or palladium.

19. The apparatus of claim 16 which further comprises a layer of gold electrodeposited on each said nanoparticle.

20. The apparatus of claim 16 wherein said enzyme is covalently bonded to said nanoparticle.

21. The apparatus of claim 16 wherein said enzyme is bonded to said nanoparticle by a thiol linker.

22. The apparatus of claim 16 wherein the substance is glucose and the enzyme is glucose oxidase.

23. The apparatus of claim 16 wherein the substance is glutamate and the enzyme is glutamate oxidase.

24. The apparatus of claim 16 wherein the substance is glutamate and the enzyme is glutamate dehydrogenase.

25. The apparatus of claim 16 wherein at least one of the products is hydrogen peroxide.

26. The apparatus of claim 16 wherein said insulating layer comprises porous anodic alumina.

27. The apparatus of claim 16 wherein a characteristic overall average length of said nanoparticles is more than about 100 nanometers and less than about 300 nanometers.

28. The apparatus of claim 16 wherein said conductive layer comprises titanium.

29. The apparatus of claim 16 wherein the carbon nanotube is a single walled carbon nanotube.

30. The apparatus of claim 16 wherein the carbon nanotube is a multiwalled walled carbon nanotube.

* * * * *